(12) United States Patent
Schweiger et al.

(10) Patent No.: US 10,136,973 B2
(45) Date of Patent: *Nov. 27, 2018

(54) LITHIUM SILICATE MATERIALS

(71) Applicant: Ivoclar Vivadent AG, Schaan (LI)

(72) Inventors: Marcel Schweiger, Chur (CH); Volker Rheinberger, Vaduz (LI); Harald Bürke, Frastanz (AT); Wolfram Höland, Schaan (LI); Elke Signer-Apel, Oberschan (CH); Christian Ritzberger, Grabs (CH); Dmitri Brodkin, Livingston, NJ (US)

(73) Assignee: Ivoclar Vivadent AG, Schaan (LI)

( * ) Notice: Subject to any disclaimer, the term of this patent is extended or adjusted under 35 U.S.C. 154(b) by 126 days.

This patent is subject to a terminal disclaimer.

(21) Appl. No.: 14/984,490

(22) Filed: Dec. 30, 2015

(65) Prior Publication Data

US 2016/0106526 A1 Apr. 21, 2016

Related U.S. Application Data

(60) Continuation of application No. 13/834,526, filed on Mar. 15, 2013, now Pat. No. 9,248,078, which is a
(Continued)

(30) Foreign Application Priority Data

Aug. 7, 2003 (DE) .................................. 103 36 913
Feb. 8, 2005 (EP) ..................................... 05002588
Jun. 20, 2005 (DE) ......................... 10 2005 028 637

(51) Int. Cl.
*C03C 10/04* (2006.01)
*A61K 6/00* (2006.01)
(Continued)

(52) U.S. Cl.
CPC .............. *A61C 13/083* (2013.01); *A61C 5/77* (2017.02); *A61C 13/0006* (2013.01);
(Continued)

(58) Field of Classification Search
CPC ... C03C 3/097; C03C 4/0021; C03C 10/0027; C03C 17/02; C03C 2217/92;
(Continued)

(56) References Cited

U.S. PATENT DOCUMENTS 2,684,911 A 7/1954 Stookey
3,022,180 A 2/1962 Morrissey et al.
(Continued)

FOREIGN PATENT DOCUMENTS

CA 2252660 5/1999
DE 2451121 5/1975
(Continued)

OTHER PUBLICATIONS

Stookey, S.D., "Chemical Machining of Photosensitive Glass," Ind. Eng. Chem. 45:115-118 (1993). Jan. 1, 1993.
(Continued)

*Primary Examiner* — C Melissa Koslow
(74) *Attorney, Agent, or Firm* — Hodgson Russ LLP

(57) ABSTRACT

Lithium silicate materials are described which can be easily processed by machining to dental products without undue wear of the tools.

4 Claims, 7 Drawing Sheets

Related U.S. Application Data division of application No. 12/833,721, filed on Jul. 9, 2010, now Pat. No. 8,444,756, which is a continuation-in-part of application No. 12/509,959, filed on Jul. 27, 2009, now Pat. No. 7,816,291, which is a continuation of application No. 11/935,203, filed on Nov. 5, 2007, now Pat. No. 8,047,021, which is a division of application No. 10/913,095, filed on Aug. 6, 2004, now Pat. No. 7,316,740, said application No. 12/833,721 is a continuation-in-part of application No. 12/253,437, filed on Oct. 17, 2008, now Pat. No. 7,871,948, which is a division of application No. 11/348,053, filed on Feb. 6, 2006, now Pat. No. 7,452,836.

(51) Int. Cl.

| | |
|---|---|
| A61C 13/083 | (2006.01) |
| C03C 3/097 | (2006.01) |
| C03C 10/00 | (2006.01) |
| A61C 13/00 | (2006.01) |
| A61K 6/02 | (2006.01) |
| A61C 13/09 | (2006.01) |
| C03B 19/02 | (2006.01) |
| C03B 32/02 | (2006.01) |
| C03C 4/00 | (2006.01) |
| C03C 17/02 | (2006.01) |
| A61C 5/77 | (2017.01) |

(52) U.S. Cl.
CPC ......... *A61C 13/0022* (2013.01); *A61C 13/09* (2013.01); *A61K 6/0205* (2013.01); *C03B 19/02* (2013.01); *C03B 32/02* (2013.01); *C03C 3/097* (2013.01); *C03C 4/0021* (2013.01); *C03C 10/0009* (2013.01); *C03C 10/0027* (2013.01); *C03C 17/02* (2013.01); *C03C 2217/92* (2013.01)

(58) Field of Classification Search
CPC ....... C03B 19/02; C03B 32/02; A61K 6/0205; A61C 13/083; A61C 13/0006; A61C 13/0022; A61C 13/09; A61C 5/77
See application file for complete search history.

(56) References Cited

U.S. PATENT DOCUMENTS

| | | |
|---|---|---|
| 3,252,778 A | 5/1966 | Goodmann et al. |
| 3,006,775 A | 10/1969 | Chen |
| 3,804,608 A | 4/1974 | Gaskell et al. |
| 3,816,704 A | 6/1974 | Borom et al. |
| 3,977,857 A | 8/1976 | Mattox |
| 4,155,888 A | 5/1979 | Mooth et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,671,770 A | 6/1987 | Bell et al. |
| 4,963,707 A | 10/1990 | Zyokou et al. |
| 4,977,114 A | 12/1990 | Horinouchi et al. |
| 5,176,961 A | 1/1993 | Crooker et al. |
| 5,219,799 A | 6/1993 | Beall et al. |
| 5,432,130 A | 7/1995 | Rheinberger et al. |
| 5,507,981 A | 4/1996 | Petticrew |
| 5,618,763 A | 4/1997 | Frank et al. |
| 5,628,564 A | 5/1997 | Nenyel |
| 5,691,256 A | 11/1997 | Taguchi et al. |
| 5,698,019 A | 12/1997 | Frank et al. |
| 5,698,482 A | 12/1997 | Frank |
| 5,702,514 A | 12/1997 | Petticrew |
| 5,707,777 A | 1/1998 | Aoai et al. |
| 5,872,069 A | 2/1999 | Abe |
| 5,874,376 A | 2/1999 | Taguchi et al. |
| 5,938,959 A | 8/1999 | Wang |
| 5,968,856 A | 10/1999 | Schweiger et al. |
| 6,066,584 A | 5/2000 | Krell et al. |
| 6,095,682 A | 8/2000 | Hollander |
| 6,106,747 A | 8/2000 | Wohlwend |
| 6,121,175 A | 9/2000 | Drescher et al. |
| 6,048,589 A | 11/2000 | Suzuki |
| 6,157,004 A | 12/2000 | Bizzio |
| 6,163,020 A | 12/2000 | Bartusch et al. |
| 6,174,827 B1 | 1/2001 | Goto |
| 6,252,202 B1 | 6/2001 | Zychek |
| 6,267,595 B1 | 7/2001 | Gratz |
| 6,270,876 B1 | 8/2001 | Abe et al. |
| 6,287,121 B1 | 9/2001 | Guiot et al. |
| 6,342,458 B1 | 1/2002 | Schweiger et al. |
| 6,376,397 B1 | 4/2002 | Petticrew |
| 6,420,288 B2 * | 7/2002 | Schweiger ............ C03C 4/0021 106/35 |
| 6,441,346 B1 | 8/2002 | Zychek |
| 6,455,451 B1 | 9/2002 | Brodkin et al. |
| 6,485,849 B2 | 11/2002 | Petticrew |
| 6,517,623 B1 | 2/2003 | Brodkin et al. |
| 6,514,893 B1 | 4/2003 | Schweiger et al. |
| 6,593,257 B1 | 7/2003 | Nagata |
| 6,802,894 B2 | 10/2004 | Brodkin et al. |
| 6,818,573 B2 | 11/2004 | Petticrew |
| 7,162,321 B2 | 1/2007 | Luthardt et al. |
| 7,316,740 B2 | 1/2008 | Schweiger et al. |
| 7,452,836 B2 | 11/2008 | Apel et al. |
| 7,655,586 B1 | 2/2010 | Brodkin et al. |
| 7,806,694 B2 | 10/2010 | Brodkin et al. |
| 7,816,291 B2 | 10/2010 | Schweiger et al. |
| 7,867,930 B2 * | 1/2011 | Apel ................ C03B 32/02 106/35 |
| 7,867,933 B2 | 1/2011 | Apel et al. |
| 7,871,948 B2 | 1/2011 | Apel et al. |
| 7,892,995 B2 | 2/2011 | Castillo |
| 7,993,137 B2 | 8/2011 | Apel et al. |
| 8,042,358 B2 * | 10/2011 | Schweiger .......... C03C 10/0027 65/33.1 |
| 8,047,021 B2 * | 11/2011 | Schweiger .......... C03C 10/0027 65/33.1 |
| 8,444,756 B2 | 5/2013 | Schweiger et al. |
| 9,248,078 B2 * | 2/2016 | Schweiger ............ C03C 3/097 |
| 2001/0006174 A1 | 7/2001 | Brennan |
| 2002/0009600 A1 | 1/2002 | Peng |
| 2002/0010063 A1 | 1/2002 | Schweiger et al. |
| 2002/0022563 A1 | 2/2002 | Schweiger et al. |
| 2002/0031670 A1 | 3/2002 | Goto et al. |
| 2002/0035025 A1 | 3/2002 | Schweiger et al. |
| 2004/0182538 A1 | 9/2004 | Lambrecht |
| 2005/0098064 A1 | 5/2005 | Schweiger et al. |
| 2005/0127544 A1 | 6/2005 | Brodkin et al. |
| 2006/0082033 A1 | 4/2006 | Hauptmann et al. |
| 2006/0257823 A1 | 11/2006 | Pfeiffer et al. |
| 2006/0257824 A1 | 11/2006 | Pfeiffer et al. |
| 2007/0023971 A1 | 2/2007 | Saha et al. |
| 2008/0120994 A1 | 5/2008 | Schweiger et al. |
| 2008/0199823 A1 | 8/2008 | Miller |
| 2009/0023574 A1 | 1/2009 | Holand et al. |
| 2009/0038344 A1 | 2/2009 | Apel et al. |
| 2009/0038508 A1 | 2/2009 | Apel et al. |
| 2009/0042166 A1 | 2/2009 | Craig et al. |
| 2009/0256274 A1 | 10/2009 | Castillo |
| 2009/0258778 A1 | 10/2009 | Castillo |
| 2010/0083706 A1 | 4/2010 | Castillo |
| 2011/0030423 A1 | 2/2011 | Johannes et al. |
| 2011/0256409 A1 | 10/2011 | Ritzberger et al. |
| 2012/0094822 A1 | 4/2012 | Castillo |
| 2012/0148988 A1 | 6/2012 | Castillo |
| 2012/0248642 A1 | 10/2012 | Ritzberger et al. |

FOREIGN PATENT DOCUMENTS

| | | |
|---|---|---|
| DE | 4303458 | 1/1994 |
| EP | 0231773 | 8/1987 |
| EP | 536479 | 4/1993 |

(56) References Cited

FOREIGN PATENT DOCUMENTS

| | | |
|---|---|---|
| EP | 536572 | 4/1993 |
| EP | 0817597 | 1/1998 |
| EP | 0827941 | 3/1998 |
| EP | 774933 | 6/2000 |
| EP | 1127564 | 8/2001 |
| EP | 1152641 | 11/2001 |
| EP | 1505041 | 2/2005 |
| EP | 1688398 | 8/2006 |
| GB | 752243 | 7/1956 |
| GB | 2284655 | 6/1995 |
| JP | 10323354 | 12/1998 |
| JP | 11074418 | 3/1999 |
| JP | 2005062832 | 3/2005 |
| WO | 199532678 | 12/1995 |
| WO | 0228802 | 4/2002 |
| WO | 2006042046 | 4/2006 |
| WO | 2007028787 | 3/2007 |
| WO | 2012143137 | 10/2012 |

OTHER PUBLICATIONS

Montedo et al., Low Thermal Expansion Sintered LZSA Glass Ceramics, American Ceramic Society Bulletin, vol. 87, Issue 7, pp. 34-40. Jul. 1, 2008.

Von Clausburch et al., "The effect of P2O5 on the Crystallization and Microstructure of Glass-Ceramics in the Si02—Li02—K2O—ZnO—P2O5 System," J. of Non-Crystalline Solids 263&264, pp. 388-394 (2000). Jan. 1, 2000.

Giassi et al., "Injection Moulding of LiO2—ZrO2—SiO2—Al2O3 (LZSA) Glass Ceramics," Glass Technol., 46(3), 277-280 (2005). Jan. 1, 2005.

Borom, et al., "Strength and Microstructure in Lithium Disilicate Glass Ceramics," J. Am. Ceram. Soc. 58 (9-10): 285-391 (1975). Jan. 1, 1975.

de Oliveira et al., "Sintering and Crystalization of a Glass Powder in the Li2O—ZrO2—SiO2 System," J. Am. Ceramic Soc. 81(3):777-780 (1998). Jan. 1, 1998.

Von Clausburch et al., "Effect of ZnO on the Crystallization, Microstructure, and Properties of Glass-Ceramics in the SiO2=Li2O—K2O—P2O5 System," Glastech. Ber. Glass. Sci. Technol. 74(8):223-229 (2001). Jan. 1, 2001.

European Search Report for EP Application No. 101718393, dated Jan. 25, 2011 Jan. 25, 2011.

http://en.wikipedia.org/wiki/Nucleation Sep. 20, 2012.

Apel et al., Influence of Zr02 on the crystallization and properties of lithium disilicate glass-ceramics derived from multi-component system, Journal of European Ceramic Society, 2007, 27, 1571-1577. Jan. 1, 2007.

McMillan et al., The Structure and Properties of a Lithium Zinc Silicate Glass-Ceramic, Journal of Material Science 1966, I. 269-279. Jan. 1, 1966.

Deubener et al., Induction time analysis of nucleation and crystal grown in di- and metasilicate glasses, Journal of Non-Crystalline Solids 1993, 163, 1-12. Jan. 1, 1993.

Holand et al., Glass-ceramic technology, American Chemical Society 2002, Westerville OH, USA. Jan. 1, 2002.

Holand et al., Control of nucleation in glass ceramics, Phil. Trans. Soc. Lond. A 2003, 361, 575-589. Jan. 1, 2003.

Holand et al., Principles and phenomena of bioengineering with glass-ceramics of dental restoration, Journal of the Europaen Ceramics Society 2007, 27, 1571-1577. Jan. 1, 2007.

Ivoclar Vivadent, Inc., IPS e.max lithium disilicate, 627329, Rev. Feb. 2009. Feb. 1, 2009.

Durschang, Report of Results, Fraunhofer Institute for Silicate Research ISC Glass and Mineral Materials, 2015. Jan. 1, 2015.

\* cited by examiner

LITHIUM SILICATE MATERIALS

This application is a continuation of U.S. patent application Ser. No. 13/834,526, filed Mar. 15, 2013, now U.S. Pat. No. 9,248,078, which is a divisional application of U.S. patent application Ser. No. 12/833,721, filed Jul. 9, 2010, now U.S. Pat. No. 8,444,756, which is a continuation-in-part application of U.S. patent application Ser. No. 12/509,959, filed Jul. 27, 2009, now U.S. Pat. No. 7,816,291 which is a continuation of U.S. patent application Ser. No. 11/935,203, filed Nov. 5, 2007, now U.S. Pat. No. 8,047,021 which is a division of U.S. patent application Ser. No. 10/913,095, filed Aug. 6, 2004, now U.S. Pat. No. 7,316,740, which claims priority to German Patent Application No. 103 36 913, filed Aug. 7, 2003, and U.S. patent application Ser. No. 12/833,721, filed Jul. 9, 2010, now U.S. Pat. No. 8,444,756 is also a continuation-in-part application of U.S. patent application Ser. No. 12/253,437, filed Oct. 17, 2008, now U.S. Pat. No. 7,871,948, which is a division of U.S. patent application Ser. No. 11/348,053, filed Feb. 6, 2006, now U.S. Pat. No. 7,452,836, which claims priority to European Patent Application No. EP 05002588, filed Feb. 8, 2005, and German Patent Application No. 10 2005 028 637, filed Jun. 20, 2005, all of which are herein incorporated by reference in their entirety.

This application is related to U.S. patent application Ser. No. 12/562,348, filed Sep. 18, 2009, now U.S. Pat. No. 7,955,159, which is herein incorporated by reference in its entirety.

The invention relates to lithium silicate materials which can be easily shaped by machining and subsequently converted into shaped products with high strength.

There is an increasing demand for materials which can be processed into dental restorative products, such as crowns, inlays and bridges, by means of computer controlled milling machines. Such CAD/CAM methods are very attractive as they allow providing the patient quickly with the desired restoration. A so-called chair-side treatment is thus possible for the dentist.

However, materials suitable for processing via computer aided design/computer aided machining (CAD/CAM) methods have to meet a very specific profile of properties.

First of all, they need to have in the finally prepared restoration appealing optical properties, such as translucence and shade, which imitate the appearance of the natural teeth. They further need to show high strength and chemical durability so that they can take over the function of the natural tooth material and maintain these properties over a sufficient period of time while being permanently in contact with fluids in the oral cavity which can even be aggressive, such as acidic in nature.

Secondly and very importantly, it should be possible to machine them in an easy manner into the desired shape without undue wear of the tools and within short times. This property requires a relatively low strength of the material and is therefore in contrast to the desired properties mentioned above for the final restoration.

The difficulty of combining the properties of low strength in the stage of the material to be processed and a high strength of the final restoration is reflected by the known materials for a CAD/CAM processing which are in particular with respect to an easy machinability unsatisfactory.

DE-A-197 50 794 discloses lithium disilicate glass ceramics which are primarily intended to be shaped to the desired geometry by a hot-pressing process wherein the molten material is pressed in the viscous state. It is also possible for these materials to be shaped by computer aided milling processes. However, it has been shown that the machining of these materials results in a very high wear of the tools and very long processing times. These disadvantages are caused by the high strength and toughness primarily imparted to the materials by the lithium disilicate crystalline phase. Moreover, it has been shown that the machined restorations show only poor edge strength. The term "edge strength" refers to the strength of parts of the restoration having only a small thickness in the range of few 1/10 mm.

Further approaches of achieving easy machinability together with a high strength of the final restoration have also been made. EP-B-774 993 and EP-B-817 597 describe ceramic materials on the basis of $Al_2O_3$ or $ZrO_2$ which are machined in an unsintered state which is also referred to as "green state". Subsequently, the green bodys are sintered to increase the strength. However, these ceramic materials suffer from a drastical shrinkage of up to 50% by volume (or up to 30% as linear shrinkage) during the final sintering step. This leads to difficulties in preparing the restorations with exactly the dimensions as desired. The substantial shrinkage represents a particular problem if complicated restorations are manufactured, such as a multi-span bridge.

From S. D. Stookey: "Chemical Machining of Photosensitive Glass", *Ind. Eng. Chem.*, 45, 115-118 (1993) and S. D. Stookey: "Photosensitivity Opacifiable Glass" U.S. Pat. No. 2,684,911 (1954) it is also known that in lithium silicate glass ceramics a metastable phase can be formed at first. For example in photosensitive glass ceramics (Fotoform®, Foto-Ceram®) Ag-particles are formed using UV-light. These Ag-particles serve as crystallization agent in a lithium metasilicate phase. The areas which were exposed to light are in a subsequent step washed out by diluted HF. This procedure is possible since the solubility of the lithium metasilicate phase in HF is much higher than the solubility of the parent glass. The glass portion remaining after said solubilizing process (Fotoform®) can be transferred into a lithium disilicate glass ceramic (FotoCeram®) by an additional heat treatment.

Also investigations of Borom, e.g. M.-P. Borom, A. M. Turkalo, R. H. Doremus: "Strength and Microstructure In Lithium Disilicate Glass-Ceramics", *J. Am. Ceream. Soc.*, 58, No. 9-10, 385-391 (1975) and M.-P. Borom, A. M. Turkalo, R. H. Doremus: "Verfahren zum Herstellen von Glaskeramiken" DE-A-24 51 121 (1974), show that a lithium disilicate glass ceramic can in the first instance crystallize in varying amounts as metastable lithium metasilicate phase. However, there also exist compositions which crystallize in the form of the disilicate phase from the beginning and the metasilicate phase is not present at all. A systematic investigation of this effect has not become known. From the investigations of Borom it is also known that the glass ceramic which contains lithium metasilicate as the main phase has a reduced strength compared to the one of a glass ceramic which only contains a lithium disilicate phase.

U.S. Publication Nos. 2009/0258778, 2009/0256274 and 2010/0083706 to Castillo, which are hereby incorporated by reference, are directed to lithium silicate glass ceramics, comprising lithium metasilicate crystals formed by heat treatment at 630° to 650° C. for 10 to 40 minutes. In Castillo, nucleation and crystal growth are occurring simultaneously. Nevertheless, the metasilicate block or ingot of Castillo which is termed pre-nucleated or nucleated, has a strength from 99-145 MPa. In Castillo, the dental restoration is made from the intermediate block or ingot either by CAD/CAM milling and fully crystallizing it from 830° to 870° C. or by hot pressing at a temperature from 800° to 870° C.

Thus, the prior art materials show a couple of shortcomings. It is, therefore, an object of the present invention to eliminate these disadvantages and in particular to provide a material which, above all, can be easily shaped by computer-aided milling and trimming processes and can subsequently be converted into high-strength dental products which also display a high chemical durability and excellent optical properties and exhibit a drastically reduced shrinkage during said final conversion.

This object is achieved by the lithium silicate glass ceramic material herein described and as set forth in the claims, hereby incorporated into the specification.

The invention also relates to a lithium disilicate material, a dental product, processes for the preparation of a lithium silicate blank and a dental restoration according to, a lithium silicate glass, a blank, and to methods for manufacturing a lithium silicate restoration or a dental restoration.

Figure 1:
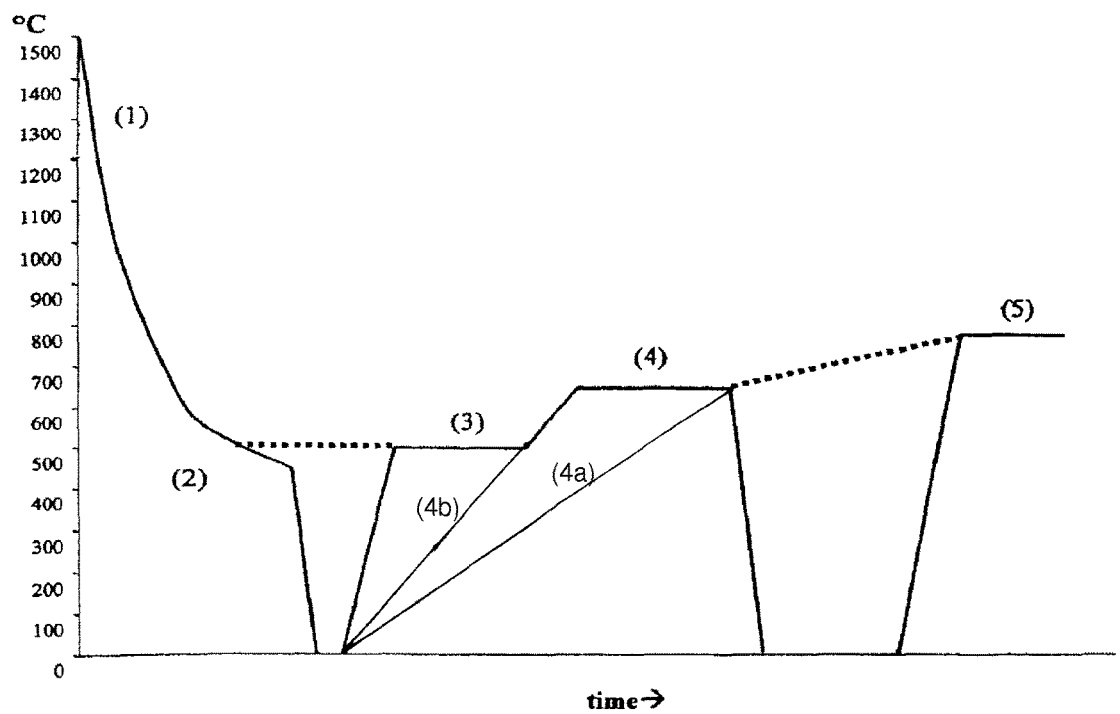
FIG. 1 shows a principle temperature profile of a process according to the invention starting from the melt via lithium metasilicate to lithium disilicate with options (4a) and (4b) for nucleation and crystallization.

It has surprisingly been shown that by using a starting glass of a very specific composition and a specific process it is possible to provide the glass ceramic according to the invention which has metastable lithium metasilicate ($Li_2SiO_3$) as main crystalline phase rather than lithium disilicate ($Li_2Si_2O_5$). This lithium metasilicate glass ceramic has a low strength and toughness and hence can be easily machined into the shape of even complicated dental restorations, but can after such machining be converted by a heat treatment into a lithium disilicate glass ceramic product with outstanding mechanical properties, excellent optical properties and very good chemical stability thereby undergoing only a very limited shrinkage.

The lithium silicate glass ceramic material according to the invention comprises the following components

| Component | Wt. % |
|---|---|
| $SiO_2$ | 64.0-73.0 |
| $Li_2O$ | 13.0-17.0 |
| $K_2O$ | 2.0-5.0 |
| $Al_2O_3$ | 0.5-5.0 |
| $P_2O_5$ | 2.0-5.0 | and comprises lithium metasilicate as main crystalline phase.

Another preferred embodiment of the present invention is formed by a silicate glass ceramic material as described above which is formed in a process which includes a step wherein lithium metasilicate as main crystalline phase is produced.

It is preferred that the lithium silicate material of the present invention further comprises the following additional components independently from each other

| Component | Wt. % |
|---|---|
| ZnO | 0.5-6.0, preferably 2.0-6.0 |
| $Na_2O$ | 0.0-2.0 |
| $Me^{II}O$ | 0.0-7.0, preferably 0.0-5.0 |
| $ZrO_2$ | 0.0-2.0 |
| colouring and fluorescent metal oxides | 0.5-7.5 | with $Me^{II}O$ being one or more members selected from the group consisting of CaO, BaO, SrO and MgO.

A lithium silicate material which comprises the following components, independently of one another, in the following amounts is particularly preferred:

| Component | Wt. % |
|---|---|
| $SiO_2$ | 65.0-70.0 |
| $Li_2O$ | 14.0-16.0 |
| $K_2O$ | 2.0-5.0 |
| $Al_2O_3$ | 1.0-5.0 |
| $P_2O_5$ | 2.0-5.0 |
| ZnO | 2.0-6.0 |
| $Na_2O$ | 0.1-2.0 |
| $Me^{II}O$ | 0.1-7.0, preferably 0.1-5.0 |
| $ZrO_2$ | 0.1-2.0 |
| coloring and fluorescent metal oxides | 0.5-3.5 | with $Me^{II}O$ being one or more members selected from the group consisting of CaO, BaO, SrO and MgO, and with the metal of the one or more coloring and fluorescent metal oxides being preferably selected from the group consisting of Ta, Tb, Y, La, Er, Pr, Ce, Ti, V, Fe and Mn.

The phrase " . . . independently from each other . . . " means that at least one of the preferred amounts is chosen and that it is therefore not necessary that all components are present in the preferred amounts.

As colouring components or fluorescent components for example oxides of f-elements may be used, i.e. the list of metals given above is not to be seen as terminal. The colouring or fluorescent components ensure that the colour of the final dental product matches that of the natural tooth material of the patient in question.

In the above composition $P_2O_5$ acts as a nucleation agent for the lithium metasilicate crystals and a concentration of at least 2 wt % is required for the necessary nucleation. Instead of $P_2O_5$, other nucleation agents are also possible, e.g. compounds of the elements Pt, Ag, Cu and W.

In addition to the components mentioned above the glass ceramic may further comprise additional components to enhance the glass technical processability. Such additional components may therefore be in particular compounds such as $B_2O_3$ and F which in general amount to 0 to 5.0% by weight.

A lithium silicate material as described above is particularly preferred which comprises 67.0 to 70.0 wt % of $SiO_2$.

It has surprisingly been shown that a specific volume portion of lithium metasilicate should be present to achieve excellent processing properties. Thus, it is further preferred that the lithium metasilicate crystalline phase forms 20 to 50 vol % and in particular 30 to 40 vol % of the lithium silicate material. Such a part of the volume leads to the crystals being present rather remote from each other and hence avoids a too high strength of the lithium silicate material.

Lithium silicate material of higher crystallinity, i.e., comprising higher volume percent of metasilicate phase or combinations of metasilicate phase with disilicate phase can be produced for some compositional ranges by heat treating at higher temperatures such as 700° C. (Cycle B) as set forth in U.S. Pat. No. 7,452,836 to Apel et al., compared to 650° C. in U.S. Pat. No. 7,316,740 to Schweiger et al. Such materials are also machinable by larger milling machines, such as DCS Precimill (DCS Switzerland).

The lithium metasilicate crystals are preferably of lamellar or platelet form. This leads to a very good machinability of the lithium silicate material without use of high energy and without uncontrolled breaking. The latter aspect of uncontrolled breaking is for example known from glasses which are generally unsuitable for machining. It is assumed that the preferred morphology of the lithium metasilicate crystals is also responsible for the surprisingly high edge strength of products, e.g. complicated dental restorations, can be made from the lithium silicate material according to the invention.

The lithium silicate material according to the invention preferably is in the form of a blank. The blank usually takes the form of a small cylinder or a rectangular block. The exact form depends on the specific apparatus used for the desired computer-aided machining of the blank.

After the machining, the lithium silicate material according to the invention has preferably the shape of a dental restoration, such as an inlay, an onlay, a bridge, an abutment, a facing, a veneer, a facet, a crown, a partial crown, a framework or a coping.

A lithium disilicate material which is formed in a process which includes a step wherein a phase comprising primarily crystalline lithium metasilicate is produced, the lithium metasilicate being subsequently converted to lithium disilicate forms a preferred embodiment of the invention.

A dental product made from lithium disilicate, said lithium disilicate being formed in a process which includes a step wherein a phase comprising primarily crystalline lithium metasilicate is produced, the lithium metasilicate being subsequently converted to lithium disilicate forms another preferred embodiment of the present invention.

A blank of lithium silicate glass ceramic material according to the invention is preferably prepared by a process which comprises (a) producing a melt of a starting glass containing the initial components $SiO_2$, $Li_2O$, $K_2O$, $Al_2O_3$ and $P_2O_5$ as the main components, (b) pouring the melt of the starting glass into a mould to form a starting glass blank and cooling the glass blank to room temperature, (c) subjecting the starting glass blank to a first heat treatment at a first temperature to give a glass product which contains nuclei suitable for forming lithium metasilicate crystals, (d) subjecting the glass product of step (c) to a second heat treatment at a second temperature which is higher than the first temperature to obtain the lithium silicate blank with lithium metasilicate crystals as the main crystalline phase.

A process as described above, wherein the starting glass of step (a) further comprises ZnO, $Na_2O$, $Me^{II}O$, $ZrO_2$, and coloring and fluorescent metal oxides, with $Me^{II}O$ being one or more members selected from the group consisting of CaO, BaO, SrO and MgO is preferred.

A process as described above, wherein the starting glass of step (a) comprises the following initial components, independently of one another, in the following amounts

| Component | Wt. % |
|---|---|
| $SiO_2$ | 65.0-70.0 |
| $Li_2O$ | 14.0-16.0 |
| $K_2O$ | 2.0-5.0 |
| $Al_2O_3$ | 1.0-5.0 |
| $P_2O_5$ | 2.0-5.0 |
| ZnO | 2.0-6.0 |
| $Na_2O$ | 0.1-2.0 |
| $Me^{II}O$ | 0.1-7.0, preferably 0.1-5.0 |
| $ZrO_2$ | 0.1-2.0 |
| coloring and fluorescent metal oxides | 0.5-3.5 | with $Me^{II}O$ being one or more members selected from the group consisting of CaO, BaO, SrO and MgO and with the metal(s) of the one or more coloring and fluorescent metal oxides being preferably selected from the group consisting of Ta, Tb, Y, La, Er, Pr, Ce, Ti, V, Fe and Mn is even more preferred.

In step (a), a melt of a starting glass is produced which contains the components of the glass ceramic. For this purpose a corresponding mixture of suitable starting materials, such as carbonates, oxides, and phosphates, is prepared and heated to temperatures of, in particular 1300 to 1600° C., for 2 to 10 hours. In order to obtain a particularly high degree of homogeneity, the glass melt obtained may be poured into water to form glass granules and the glass granules obtained are melted again.

In step (b), the melt of the starting glass is poured into a corresponding mould, e.g. a steel mould, and cooled to room temperature to give a glass product.

The cooling is preferably conducted in a controlled manner so as to allow a relaxation of the glass and to prevent stresses in the structure associated with rapid temperature changes. As a rule, the melt is therefore poured into preheated moulds, e.g. of a temperature of about 400° C. Subsequently, the product can slowly be cooled in a furnace to room temperature.

In step (c) the starting glass product is subjected to a first heat treatment at a first temperature to cause formation of nuclei for lithium metasilicate crystals. Preferably, this first heat treatment involves a heating of the glass product for a period of 5 minutes to 1 hour at a first temperature of 450 to 550° C. In some cases it is convenient to combine step b) and step c) in order to relax the glass article and nucleate the lithium metasilicate crystals in one single heat treatment therefore a process as described above, wherein step (c) is replaced by modifying step (b) such that during the cooling process a temperature of about 450 to 550° C. is held for a period of about 5 minutes to 50 minutes to produce the glass product which contains nuclei suitable for formation of the lithium metasilicate crystals during step (b) forms a preferred embodiment of the invention.

A process as described above, wherein in step (c) the first heat treatment comprises heating the starting glass blank to a temperature of about 450 to 550° C. for a period of about 5 minutes to 1 hour forms another preferred embodiment of the invention.

Subsequently, the glass product comprising the desired nuclei is cooled to room temperature.

In the subsequent step (d), the glass product having the desired nuclei of $Li_2SiO_3$ is subjected to a second heat treatment at a second temperature which is higher than the first temperature. This second heat treatment results in the desired formation of lithium metasilicate crystals as predominant and preferably as only crystalline phase and therefore gives the lithium metasilicate glass ceramic according to the invention. Preferably, this second heat treatment of step (d) comprises heating the glass product which contains nuclei suitable for formation of lithium silicate crystals to a second temperature of about 600 to 700° C. for a period of about 10 to 30 minutes.

It has further surprisingly been shown that relatively high temperatures lead to high amounts of lithium metasilicate which in turn lead to a high amount of lithium disilicate in the third heat treatment. Such high amounts of lithium disilicate impart a high strength to the ceramic. Thus, if the emphasis is on the achieving a high strength final product, then it is advantageous to carry out the second heat treatment at 680° to 720° C., and preferably 690° to 710° C. and more preferably about 700° C.

The principle temperature profile of such a process is exemplified in FIG. 1. Already starting from the melt (1), i.e. at the end of step a) the temperature decreases for relaxation of the product in a temperature range of 500 to 450° C. (2). The temperature can then be brought to room temperature (solid line), step b), and afterwards be brought to a temperature of about 450 to 550° C. or can be kept in the temperature range of 450 to 500° C. (dotted line). In the region that is labeled with (3), step c), nucleation occurs at a temperature of 450 to 550° C. and is influenced by $P_2O_5$. Then, the glass material can be heated directly to a temperature in the range of 600 to 700° C. and kept at said temperature (4) during which time lithium metasilicate forms, step d). Subsequently the material can be cooled down (solid line) to e.g. about room temperature for grinding, milling or CAD-CAM processing and can afterwards be brought to a temperature of about 700 to 950° C. or can directly be brought to 700 to 950° C. (dotted line) at which temperature (5) the second crystallization occurs forming the lithium disilicate and where additional heat treatment or hot pressing can be undertaken.

Alternatively, steps 3 and 4 can be combined into one step as shown in FIG. 1 at step 4a, or alternatively at step 4b. That is, the nucleation and crystallization may be combined in one step in the temperature range from room temperature to about 830° C. or higher. In one embodiment, the one or more heat treatments to convert the glass blanks into machinable glass-ceramic blanks is/are performed in the temperature range of from about 450° C. to about 830° C.

Depending on the specific composition of a selected starting glass, it is possible for the skilled person by means of differential scanning calorimetry (DSC) and x-ray diffraction analyses to determine suitable conditions in steps (c) and (d) to result in materials having the desired morphology and size of the crystals of lithium metasilicate. To further illustrate this process FIGS. 2 to 5 together with Tables I and II in the example section indicate how the relevant data were obtained for example 13 using said measurements and are therefore obtainable in general. Moreover, these analyses allow also the identification of conditions avoiding or limiting the formation of undesirable other crystalline phases, such as of the high-strength lithium disilicate, or of cristobalite and lithium phosphate.

Subsequent to step (d), it is preferred to shape the obtained glass ceramic. This is preferably effected by step (e), wherein the lithium metasilicate glass ceramic is machined to a glass ceramic product of the desired shape, in particular the shape of a dental restoration. The machining is preferably carried out by trimming or milling. It is further preferred that the machining is controlled by a computer, in particular by using CAD/CAM-based milling devices. This allows a so-called chair-side treatment of the patient by the dentist.

It is a particular advantage of the glass ceramic according to the invention that it can be shaped by machining without the undue wear of the tools observed with the tough and high-strength prior art materials. This is in particular shown by the easy possibility to polish and trim the glass ceramics according to the invention. Such polishing and trimming processes therefore require less energy and less time to prepare an acceptable product having the form of even very complicated dental restorations.

Lithium disilicate dental restorations can be produced in many different ways. Commonly used by dental technicians are the CAD/CAM and the hot pressing technique. Dentists can use a CAD/CAM method (Cerec 2®, Cerec 3®) to produce chair-side an all ceramic lithium disilicate restoration. The final result is always a dental restoration with lithium disilicate as the main crystalline phase. For this purpose, the blank can be a lithium metasilicate glass ceramic according to the invention. The glass ceramic according to the invention can therefore be processed in both ways, by CAD/CAM or by hot-pressing, which is very advantageous for the user.

It is also possible to use for these purposes a corresponding lithium silicate glass which comprises nuclei suitable for formation of lithium metasilicate crystals. This glass is a precursor of the lithium metasilicate glass ceramic of the invention. The invention is also directed to such a glass. It is obtainable by the above process in step (c).

For manufacturing a dental restoration by the hot pressing technique a lithium silicate glass ingot having nuclei for lithium metasilicate is subjected to a heat treatment of about 700 to 1200° C. to convert it into a viscous state. The heat treatment will be conducted in a special furnace (EP 500®, EP 600®, Ivoclar Vivadent AG). The ingot is embedded in a special investment material. During the heat treatment the ingot will be crystallized. The main crystal phase is then lithium disilicate. The viscous glass ceramic flows under a pressure of 1 to 4 MPa into the cavity of the investment material to obtain the desired shape of the dental restoration. After cooling the investment mould to room temperature the lithium disilicate restoration can be divested by sand blasting. The framework can be further coated with a glass or a glass ceramic by sintering or hot pressing technique to get the finalized dental restoration with natural aesthetics.

An ingot which comprises the lithium silicate glass ceramic according to the invention is subjected to a heat treatment of about 700 to 1200° C. to convert it into a viscous state. The heat treatment will be conducted in a special furnace (EP 500®, EP 600®, Ivoclar Vivadent AG). The glass ceramic ingot is embedded in a special investment material. During the heat treatment the glass ceramic will be further crystallized. The main crystal phase is then lithium disilicate. The viscous glass ceramic flows under a pressure of 1 to 4 MPa into the cavity of the investment material to obtain the desired shape of the dental restoration. After cooling the investment mould to room temperature the lithium disilicate restoration can be divested by sand blasting. The framework can be further coated with a glass or a glass ceramic by sintering or hot pressing technique to get the finalized dental restoration with natural aesthetics.

For manufacturing a dental restoration by the CAD/CAM technique the lithium silicate or the lithium metasilicate blocks with lithium disilicate as possible minor crystalline phase having a strength of about 80 to 150 MPa can be easily machined in a CAM unit like Cerec 2® or Cerec 3® (Sirona, Germany). Larger milling machines such as DCS Precimill® (DCS, Switzerland) are also suitable. The block is therefore positioned in the grinding chamber by a fixed or integrated holder. The CAD construction of the dental restoration is done by a scanning process or an optical camera in combination with a software tool. The milling process needs for one unit 10 to 15 minutes. Copy milling units such as Celay® (Celay, Switzerland) are also suitable for machining the blocks. First, a 1:1 copy of the desired restoration is fabricated in hard wax. The wax model is then mechanically scanned and 1:1 mechanically transmitted to the grinding tool. The grinding process is therefore not controlled by a computer. The milled dental restoration has to be subjected to a heat treatment to get the desired lithium disilicate glass ceramic with high strength and tooth like color. The heat treatment is conducted in the range of 700 to 900° C. for a period of about 5 to 30 minutes. The framework can be further coated with a glass or a glass ceramic by sintering or hot pressing technique to get the finalized dental restoration with natural aesthetics.

Blocks stronger than about 180-200 MPa and having upward strengths as high as 400 MPa or greater, such as blocks comprising more than about 40% lithium metasilicate, lithium disilicate or combinations thereof are preferably grinded in a large milling machine such as DCS Precimill® (DCS, Switzerland) due to the high strength and toughness of the glass ceramic. Grinding such strong blocks in smaller milling machines may be economically prohibitive due to long milling times or increased tool wear. The block is therefore positioned in the grinding chamber by a fixed metal holder. The CAD construction of the dental restoration is done by a scanning process in combination with a software tool. An additional heat treatment in the range of 700 to 900° C. could be conducted in order to close surface flaws which were induced by the grinding process. The framework can be further coated with a glass or a glass ceramic by sintering or hot pressing technique to get the finalized dental restoration with natural aesthetics.

For blocks containing lithium metasilicate, it has been found that even at high strengths, e.g., about 200 to about 400 MPa range or more, the blocks can be milled on various types of milling machines due to the lower fracture toughness, for example, fracture toughness up to 2.0, preferably up to 1.5. In this way, the milled article or restoration may be used as is, or may be further heat treated to grow larger metasilicate or crystallize to lithium disilicate.

It has further been shown that the easily machinable lithium metasilicate glass ceramic according to the invention can be converted into a lithium disilicate glass ceramic product by a further heat treatment. The obtained lithium disilicate glass ceramic has not only excellent mechanical properties, such as high strength, but also displays other properties required for a material for dental restorations.

Thus, the invention also relates to a process for preparing a lithium metasilicate glass ceramic, which may be milled as lithium metasilicate and used as is, or further heat treated to grow more or larger metasilicate. The milled restoration is further finished by staining, glazing or veneering with overlay porcelain associated with firing at temperatures within the range of about 350° to about 850° C. Heat treatment to increase crystallinity or convert to disilicate can be done concurrently with the latter finishing/firing steps.

The invention also relates to a process for preparing a lithium disilicate glass ceramic product, which comprises (f) subjecting the lithium metasilicate glass ceramic according to the invention to a third heat treatment to convert lithium metasilicate crystals to lithium disilicate crystals.

In this step (f), a conversion of the metastable lithium metasilicate crystals to lithium disilicate crystals is effected. Preferably, this third heat treatment involves a complete conversion into lithium disilicate crystals and it is preferably carried out by heating at 700 to 950° C. for 5 to 30 minutes. The suitable conditions for a given glass ceramic can be ascertained by conducting XRD analyses at different temperatures.

It was also found out that the conversion to a lithium disilicate glass ceramic is associated with only a very small linear shrinkage of only about 0.2 to 0.3%, which is almost negligible in comparison to a linear shrinkage of up to 30% when sintering ceramics.

A process as described above, wherein the lithium silicate blank has a biaxial strength of at least 90 MPa and a fracture toughness of at least 0.8 MPam$^{0.5}$ is preferred.

A process as described above, wherein the starting glass blank of step (b), the glass product containing nuclei suitable for forming lithium metasilicate of step (c), or the lithium silicate blank with lithium metasilicate as the main crystalline phase of step (d) is shaped to a desired geometry by machining or by hot pressing to form a shaped lithium silicate product is also preferred.

Such a process, wherein the shaped lithium silicate blank is a dental restoration is more preferred and a process wherein the dental restoration is an inlay, an onlay, a bridge, an abutment, a facing, a veneer, a facet, a crown, a partial crown, a framework or a coping is even more preferred.

A process as described above, wherein the machining is performed by grinding or milling forms a preferred embodiment of the invention, whereby a process wherein the machining is controlled by a computer is even more preferred.

A process as described above but further comprising subjecting the shaped lithium silicate product to a third heat treatment at a third temperature of about 700 to 950° C. for a period of about 5 to 30 minutes is another aspect of the present invention and said process is particularly preferred when the lithium silicate product subjected to the third heat treatment comprises lithium metasilicate as the main crystalline phase, and wherein the third heat treatment converts the lithium metasilicate crystals to lithium disilicate crystals as the main crystalline phase of the dental restoration.

A process as described above wherein the lithium silicate product subjected to the third heat treatment comprises the glass product containing nuclei suitable for forming lithium metasilicate crystals, and wherein lithium disilicate crystals are crystallized directly from the nuclei suitable for forming lithium metasilicate crystals is also preferred.

Another preferred embodiment of the present invention is a process as described above, wherein the shrinkage that occurs during the third heat treatment is less than 0.5%, preferably less than 0.3%, by volume.

A process as described above which comprises shaping of a lithium silicate material to the desired geometry by hot pressing to produce the dental restoration is also an object of the invention, with a process for manufacturing a dental restoration as described above being preferred wherein the hot pressing comprises subjecting the lithium silicate material to a heat treatment at a temperature of about 500 to 1200° C. to convert the lithium silicate material into a viscous state and pressing the viscous lithium silicate material under a pressure of about 1 to 4 MPa into a mould or dye to obtain the dental restoration with a desired geometry.

A process as described above, wherein the lithium silicate material subjected to the heat treatment and pressing comprises lithium metasilicate crystals which are converted into lithium disilicate crystals during the heat treatment and pressing is more preferred.

A further preferred embodiment of the present invention is formed by a process as described above which comprises an increasing of strength and fracture toughness of the lithium silicate material.

A process for the manufacture of a dental restoration as described above is preferred, wherein the dental restoration has a biaxial strength of at least 250 MPa and a fracture toughness of at least 1.5 MPam$^{0.5}$.

A process for the manufacture of a dental restoration as described above further comprising finishing the dental restoration to obtain a natural appearance is preferred.

Same is true for a process as described above, wherein the finishing step comprises applying a coating to the dental restoration by layering with powdered materials or by hot pressing a coating material onto the unfinished dental restoration.

A process as described above wherein the third heat treatment occurs during a firing of the layering materials or the hot pressing of the coating material onto unfinished the dental restoration is even more preferred.

Thus, a product is finally obtained which has all the beneficial mechanical, optical and stability properties making lithium disilicate ceramics attractive for use as dental restorative materials. However, these properties are achieved without the disadvantages of the conventional materials when shaped by using a CAD/CAM based process, in particular the undue wear of the milling and trimming tools.

Consequently, the invention also relates to a lithium disilicate glass ceramic product which is obtainable by the above process for its preparation and has lithium disilicate as main crystalline phase. Preferably, the lithium disilicate glass ceramic product according to the invention is in the form of a dental restoration.

It is further preferred that in the lithium disilicate glass ceramic the lithium disilicate crystals form 60 to 80% by volume of the glass ceramic.

The conversion of the lithium metasilicate glass ceramic according to the invention to a lithium disilicate glass ceramic product is associated with a surprisingly high increase in strength by a factor of up to about 4. Typically, the lithium metasilicate glass ceramic of the invention has a strength of about 100 MPa, and the conversion leads to a lithium disilicate glass ceramic having a strength of more than 400 MPa (measured as biaxial strength).

The invention is also directed to a lithium silicate blank as described above, wherein the holder is jointed and connected with the holder.

A lithium silicate blank as described above, wherein the holder is from a different material from the blank forms one embodiment of the invention.

A lithium silicate material blank as described above, wherein the holder is made from an alloy, from a metal, from a glass ceramic or from a ceramic forms a preferred embodiment of the invention.

A lithium silicate blank as described above, wherein the holder is made from the same material as the blank and is integral with the blank is another embodiment of the invention.

A lithium silicate blank as described above, wherein the blank is labeled with information is another preferred embodiment.

Same is true for a lithium silicate blank as described above, wherein the information on the blank comprises the material, the size and the type of the shape, which is to be machined from the blank.

The invention is also directed to a lithium silicate glass-ceramic dental product comprising lithium metasilicate and having a flexural strength of 180 MPa or greater, for example in the range of 180 to 200 MPa to about 400 MPa or greater and a fracture toughness less than about 2.0, preferably less than about 1.5.

A process described herein for manufacture of a dental article is another object of the invention, wherein a lithium metasilicate block is fabricated having a strength of about 180 or 200 MPa to about 400 MPa and a fracture toughness less than about 2.0, preferably less than about 1.5 and milling the block into a dental restoration. The dental restoration may be used as is or further heat treated and/or coated.

Another aspect of the present invention is directed to a method for manufacturing a lithium silicate restoration comprising preparing a lithium silicate blank as described above, and thereafter coating a dental restoration with the lithium silicate blank.

A method for manufacturing a dental restoration as described above wherein a dental framework is coated by hot pressing the lithium silicate blank onto the dental framework is preferred.

A method for manufacturing a dental restoration as described above, wherein the dental framework is a crown, a partial crown, a bridge, a coping, a veneer, a facing or an abutment is more preferred and such a method, wherein the dental framework is made from a metal, an alloy, a ceramic or a glass ceramic is even more preferred.

A method for manufacturing a dental restoration as described above, wherein the ceramic comprises zirconium oxide, aluminium oxide, a zirconium mix oxide, an aluminium mix oxide, or a combination thereof forms a particularly preferred embodiment of the invention.

A method for manufacturing a dental restoration as described above wherein the lithium silicate blank which is coated onto the framework comprises lithium metasilicate crystals which are converted to lithium disilicate crystals, or the lithium silicate blank comprises nuclei suitable for forming lithium metasilicate crystals which crystallize as lithium disilicate crystals during the hot pressing of the lithium silicate blank onto the dental framework is another preferred object of the invention.

The invention is explained in more detail below on the basis of Examples.

EXAMPLES

Examples 1 to 18 (Invention), 19 to 20 (Comparison) and 21 to 23 (Invention) and 24 to 25 (Invention)

A total of 20 different lithium metasilicate glass ceramic products according to the invention as well as two ceramics for comparison with the chemical compositions given in Table III were prepared by carrying out stages (a) to (d) of the process described above and finally converted to lithium disilicate glass ceramic products by step (e) of the process described above:

For this purpose samples of the corresponding starting glasses were melted in a platinum-rhodium crucible at a temperature of 1500° C. and for a period of 3 hours (a).

The glass melts obtained were then poured into steel moulds which were preheated to 300° C. After 1 minute the glass blanks were transferred into a furnace which was preheated to a temperature between 450 and 550° C. The exact values, KB T [° C.] and KB t [min], are given for each sample in Table III. After this relaxation and nucleation process (b and c) the blocks were allowed to cool to room temperature. The nucleated samples were homogeneous and transparent.

The glass blanks, which contained nuclei for the crystallization, were then subjected to step (d), i.e. the second heat treatment, to crystallize lithium metasilicate, which means that the glass blanks were exposed to a temperature of about 650° C. for a period of about 20 minutes, except example 3, which was crystallized at 600° C.

The course of the crystallization was investigated by DSC-measurement and the resulting crystal phases were analyzed by XRD to identify the ideal conditions for this heat treatment. "Ideal conditions" in the sense of the present invention are present in case the two crystallization peaks of the meta- and the disilicate phase respectively are differing to such an extend that in the production process a neat differentiation can be implemented, i.e. when heating a sample to the first crystallization temperature it has to be secured that when reaching the desired temperature within the sample the temperature at the outer regions of the sample does not reach the second crystallization temperature, i.e. the bigger the temperature difference of the first and the second crystallization temperature is the bigger the sample mass can be.

Figure 2:
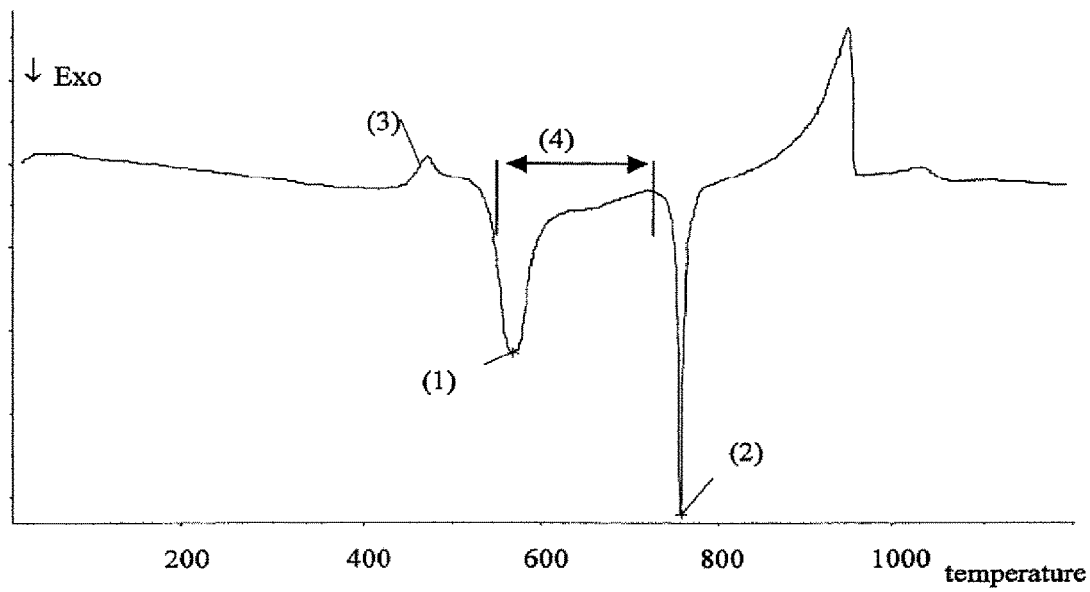
FIG. 2 shows a DSC-plot of a lithium silicate material according to example 13.

To further illustrate the process FIG. 2 shows a DSC-plot of one of the examples, example 13, a quenched and powdered glass sample, which was heated with a heating rate of 10 K/min. The crystallisation of lithium metasilicate (1), the crystallisation of lithium disilicate (2) as well as the glass transition temperature (3) and the temperature range (4) for the first crystallisation are clearly visible from said DSC-plot.

Figure 3:
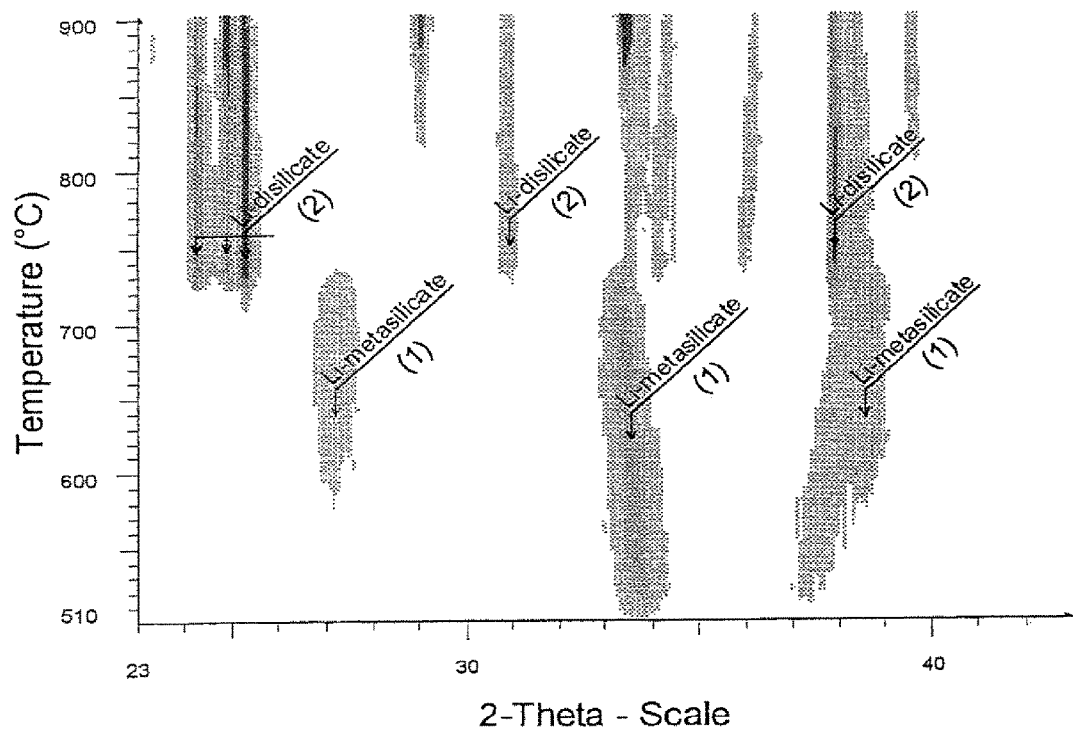
FIG. 3 shows a high temperature XRD of a lithium silicate material according to example 13, in form of a bulk glass sample.

Also an example for the analysis of phase development by high temperature XRD from the same example 13 is given. FIG. 3 therefore shows the measurement of a bulk glass sample at a constant heating rate of 2 K/min. It can be recognized from said measurement that in this case the crystallisation of the lithium metasilicate (1) occurs at a temperature of 510° C. and that in this case the resolution of the lithium metasilicate and the crystallization of the lithium disilicate (2) occur at a temperature of 730° C.

Figure 4:
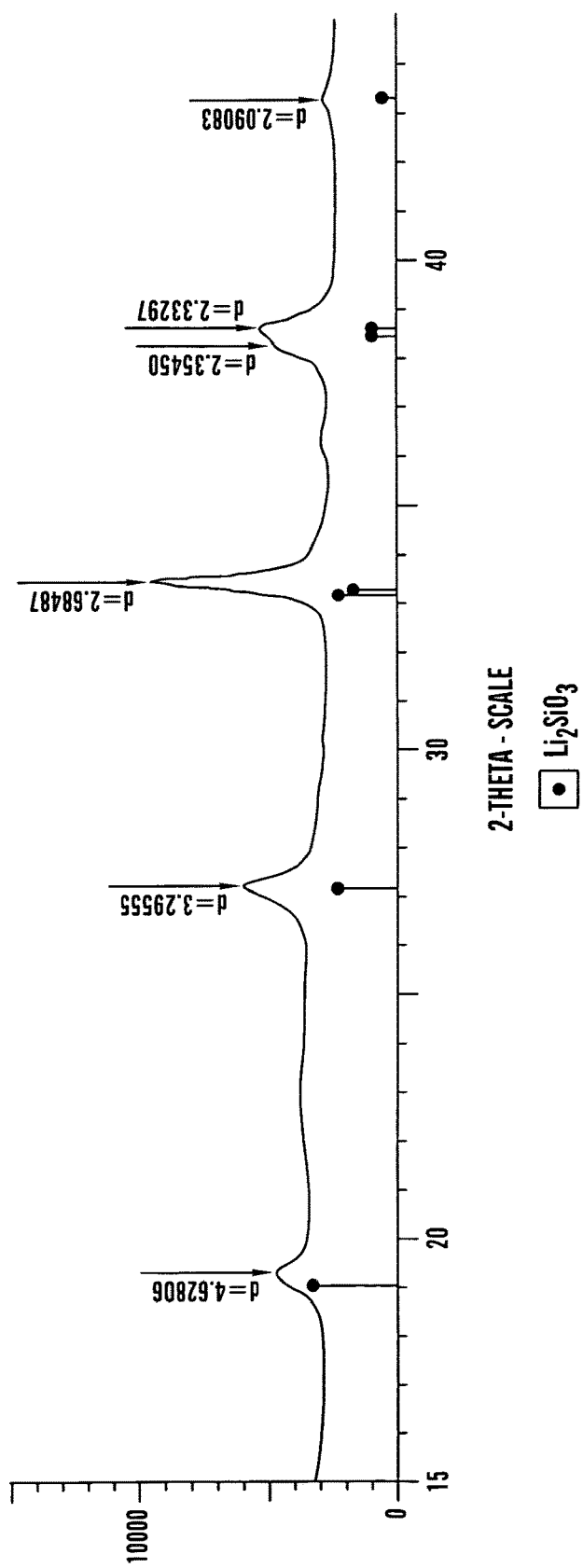
FIG. 4 shows an XRD for phase analysis of a lithium silicate material according to example 13 after nucleation and first crystallization.

FIG. 4 represents a phase analysis by XRD of example 13 after nucleation at 500° C. for 7 min and first crystallisation at 650° C. and 20 min.

The corresponding data are summarized In Table I:

TABLE I

| 1<br>d-spacing in 0.1 nm<br>of scan | 2<br>d-spacing in 0.1 nm<br>of pattern | 3<br>Index |
|---|---|---|
| 4.628 | 4.690 | LS 020 |
| 3.296 | 3.301 | LS 111 |
|  | 2.708 | LS 130 |

TABLE I-continued

| 1<br>d-spacing in 0.1 nm<br>of scan | 2<br>d-spacing in 0.1 nm<br>of pattern | 3<br>Index |
|---|---|---|
| 2.685 | 2.700 | LS 200 |
| 2.355 | 2.342 | LS 131 |
| 2.333 | 2.331 | LS 002 |

Figure 5:
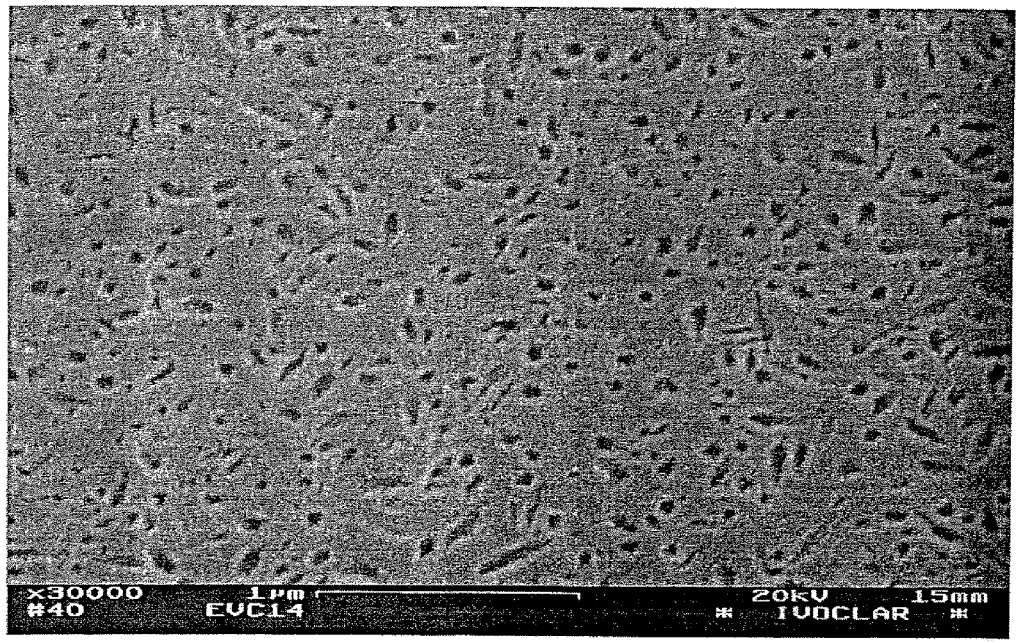
FIG. 5 shows an SEM-micrograph, back scattered electrons, of a lithium silicate material according to example 13 after nucleation and first crystallization.

FIG. 5 shows an SEM-micrograph, backscattered electrons, of the same example having the same thermal history, with the surface being etched with 1% HF for 8 s. Clearly visible are holes that show former lithium metasilicate crystals.

The resulting blocks were now ready for step (e), which means shaping the lithium metasilicate glass ceramic to the desired shape, either by saw cutting, or by milling it in a CAD-CAM milling machine (i.e. CEREC 3®). The obtained lithium metasilicate glass ceramic blanks were analyzed for their machinability and their edge strength. 10 discs were cut from a rod with 12 mm diameter for biaxial strength measurements. The results of these analyses are given in Table IV. Ten more discs were prepared and subjected to a third heat treatment (f).

In case the blanks contain colouring and fluorescent oxides the blocks in the state of the metasilicate appear to have a reddish or bluish colour. This effect vanishes when the disilicate phase forms and the blanks turn to the colour that is desired.

Finally, the lithium metasilicate glass ceramic blanks were subjected to a second crystallization, step (f), at 850° C. for 10 min, except example 3 which was crystallized at 830° C., i.e. the third heat treatment which is in general performed at temperatures of 700 to 950° C., preferably 820 to 880° C. and for a period of 5 to 30 minutes, preferably 5 to 20 minutes, to convert the lithium metasilicate into lithium disilicate. Optionally, it is not necessary to further heat treat the lithium metasilicate to convert it to lithium disilicate. It is possible to mill the dental article from the lithium metasilicate glass ceramic blanks with no further heat treatment.

Figure 6:
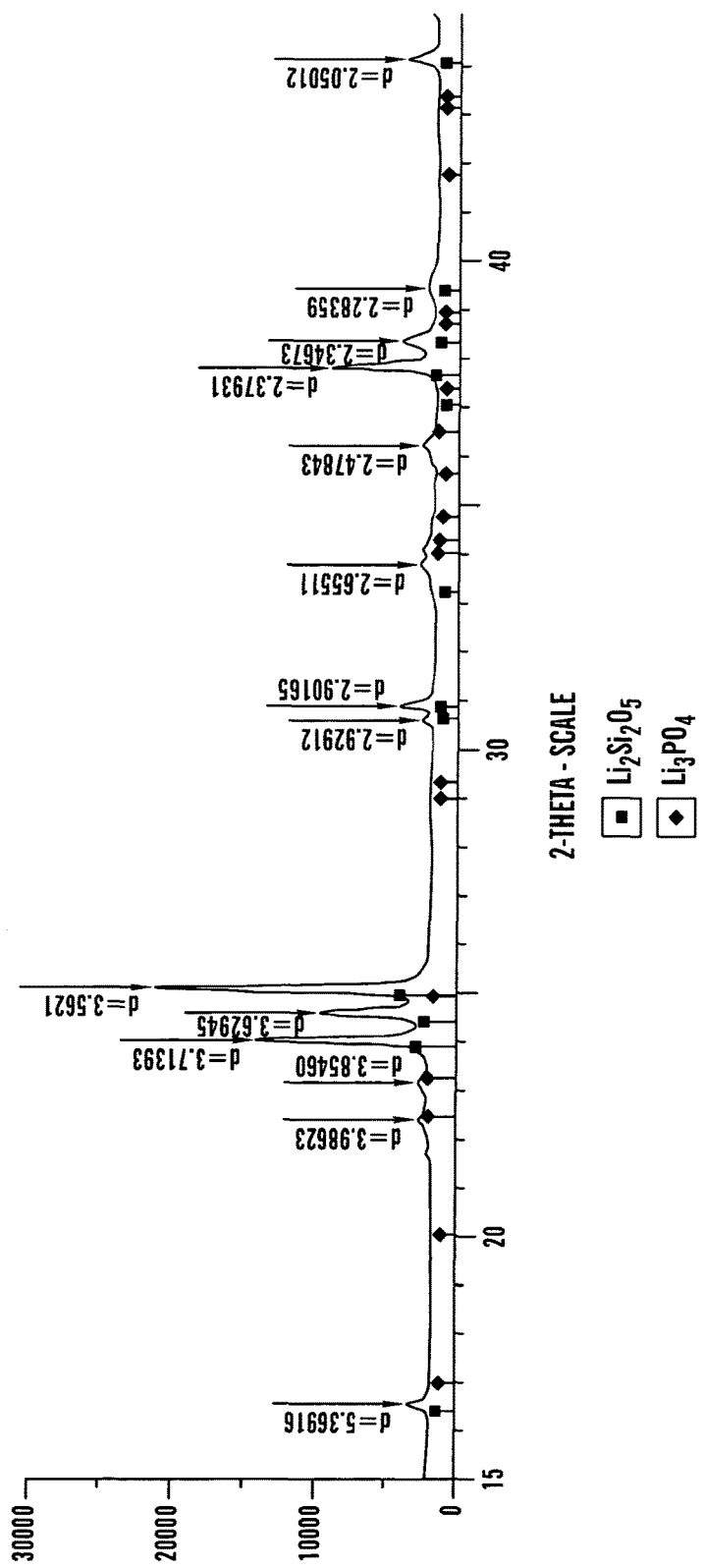
FIG. 6 shows an XRD for phase analysis of a lithium silicate material according to example 13 which was subjected to nucleation, first crystallization and second crystallization conditions.

The obtained products were analyzed for their crystal phases. To further illustrate the procedure the phase analysis for example 13 after nucleation at 500° C. for 7 min, first crystallization at 650° C. for 20 min and second crystallization at 850° C. for 10 is shown in FIG. 6. The corresponding data are summarized in Table II.

TABLE II

| 1<br>d-spacing in 0.1 nm<br>of scan | 2<br>d-spacing in 0.1 nm<br>of pattern | 3<br>Index |
|---|---|---|
| 5.369 | 5.420 | LS2 110 |
| 3.986 | 3.978 | LP 120 |
| 3.855 | 3.834 | LP 101 |
| 3.714 | 3.737 | LS2 130 |
| 3.629 | 3.655 | LS2 040 |
| 3.562 | 3.581 | LS2 111 |
| 2.929 | 2.930 | LS2 131 |
| 2.901 | 2.908 | LS2 200 |
| 2.379 | 2.388 | LS2 002 |
| 2.346 | 2.35 | LS2 221 |
| 2.283 | 2.29 | LS2 151 |
| 2.050 | 2.054 | LS2 241 |

Figure 7:
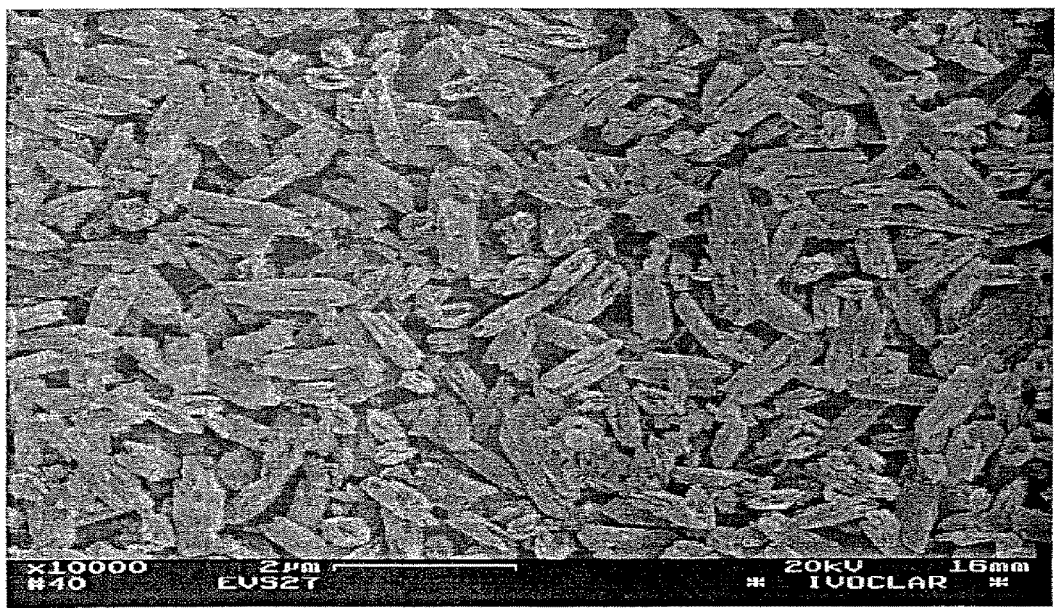
FIG. 7 shows an SEM-micrograph, back scattered electrons, of a lithium silicate material according to example 13 which was subjected to nucleation, first crystallization and second crystallization conditions and has an etched surface.

FIG. 7 shows an SEM-micrograph, backscattered electrons, of the same example having the same thermal history, with the surface being etched with 3% HF for 30 s leading to the glassy phase being etched out and leaving the lithium disilicate crystals.

In addition to the analysis in respect to crystal phases the samples were also analyzed in respect to their biaxial strength and chemical durability. Furthermore, their translucence was assessed. The results are also given in Table IV.

In table IV, the detected crystalline phases are designated as follows:
LS—lithium metasilicate
LS2—lithium disilicate
LP—lithium phosphate,
with the main phase being marked in bold type.

To gain information about the machinability tests were performed on a Cerec® 3, with new tools being used for each test. A 'Lego®-Minicube' served as a model which had to be milled from all compositions that were subjected to this test and from a leucite-enforced glass ceramic of the name ProCAD® from Ivoclar Vivadent AG. The operating sequence was as follows: First a blank of ProCAD@ was milled, then a blank of the ceramic to be tested was milled and after that again a ProCAD® blank was milled. The machinability was rendered "very good" in case the time that was required to mill the blank of the ceramic to be tested was below 95% of the time that was required to mill the ProCAD® blank. Times in the range of 95 to 105% of said time led to the mark "good" for the machinability, times in the range of 105 to 115% to "acceptable" and times above 115% to "poor". The medium time required for the milling process was 14.0 minutes.

To compare the machinability of the test samples with another glass ceramic a blank made according to the composition disclosed in DE 197 50 794 was prepared and subjected to the test described above. After 15 minutes the test was abandoned since only about 10% of the volume to be milled was already milled and the tools used for milling were already worn out, something that did not happen with any of the test samples.

The edge strength was determined as follows:
With a milling unit (CEREC 3®) blanks were milled to result in Lego-minicubes. With a 1.6 mm cylindrical diamond cutter blind holes were milled. The quality of said blind holes was determined by comparing the area of the broken out edges with those of a reference sample (ProCAD®). The relation of the area of the broken out edges to the area of the blind bore is an allocation for the edge strength.

An edge strength is considered to be "very good" in case the relation of said areas is smaller than that of the reference, it is considered to be "good" in case the relations are about the same and it is considered to be "acceptable" in case the area is bigger than 110% of the reference sample.

The chemical durability was determined according to ISO 6872, i.e. as loss of mass after 16 h in 4% acetic acid at 80° C.

"Good" means that the solubility according to said method is below 100 pg/cm$^2$.

The strength was measured as biaxial strength according to ISO 6872 or as 3 point bending strength according to EN 843-1:

Bars of 12 mm diameter were casted and crystallized once. From these bars 20 discs with a thickness of 1, 2 mm each were sawn. 10 of these discs were then smoothed and the surfaces of the discs were polished using SiC-paper of grain size 1000. Biaxial strength was measured as is disclosed in ISO 6872. The other 10 discs were crystallized a second time at 800 to 900° C. to give the lithium disilicate phase. These solidified samples were smoothed on both sides and the surfaces were polished using SiC-paper of grain size 1000. Biaxial strength was then measured according to ISO 6872.

By comparison bending strength was measured on bars with dimensions of 25*3.5*3.0 mm were sawn out of a block of the lithium metasilicate glass ceramic. These bars were smoothed to result in bars having dimensions of 25*2.5*2.0 mm which were then polished using SiC-paper of grain size 1000. The edges were also beveled with SiC-paper of grain size 1000. The span was 20 mm. The results are comparable to biaxial strength results.

In addition to this, fracture toughness was determined by applying a Vickers indentation onto a polished surface and measuring the size of the flaws originating from the edges (Indentation Force Method . . . IF). This method is useful as comparative method but does not result in absolute values. For comparison measurements were performed on notched bending samples (SENB, SEVNB). For the lithium disilicate glass ceramics fracture toughness values >2 MPam$^{0.5}$ were obtained.

In Table II the values for the biaxial strength and the fracture toughness of the samples having the disilicate phase, i.e. those samples that were crystallized twice, are given. In addition to that quotients are given which give the ratio of the biaxial strength of the disilicate system to the biaxial strength of the metasilicate system (biaxial solidification factor) or the ratio of the fracture toughness of the disilicate system to the fracture toughness of the metasilicate system (solidification factor K1C).

Translucence was determined after the second crystallization: a test piece 16 mm diameter and having a thickness of 2 mm was prepared and polished on both sides. The contrast value CR was determined according to BS 5612 (British Standard) using a spectral colorimeter (Minolta CM-3700d). The determination of the contrast value consisted of two single measurements. The test piece to be analyzed is therefor placed in front of a black ceramic body having a reflexion of 4% at most and accordingly in front of a white ceramic body having a reflexion of 86% at minimum which are then colourmetrically determined. Using highly transparent test pieces reflexion/absorption is mainly caused by the ceramic background whereas reflexion is caused by the test piece in case an opaque material is used. The ratio of reflected light on black ground to reflected light on white ground is the quantum for the contrast value, with total translucence leading to a contrast value of 0 and total opaquescence leading to a contrast value of 1. The samples were rated as follows:
extraordinary: CR<0.4
very good: 0.4<CR<0.5
good: 0.5<CR<0.6
acceptable: 0.6<CR<0.8
opaque: 0.8<CR.

TABLE III

| Expl No. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| KBT [°C.] | 500 | 490 | 520 | 500 | 500 | 500 | 500 | 500 | 500 | 500 | 520 | 500 | 500 | 500 | 500 | 500 | 500 | 500 | 500 | 500 |
| KBt [min] | 10 | 30 | 5 | 30 | 10 | 10 | 10 | 10 | 10 | 10 | 10 | 10 | 7 | 7 | 7 | 10 | 20 | 10 | 10 | 30 |
| wt % | | | | | | | | | | | | | | | | | | | | |
| $SiO_2$ | 69.3 | 73.0 | 64.0 | 68.1 | 70.1 | 69.0 | 68.6 | 69.9 | 68.6 | 68.8 | 70.0 | 65.7 | 67.4 | 68.4 | 65.0 | 70.0 | 70.0 | 67.8 | 68.3 | 67.7 |
| $K_2O$ | 4.3 | 4.4 | 4.2 | 4.2 | 4.5 | 4.3 | 4.3 | 4.4 | 2.0 | 5.0 | 5.0 | 4.1 | 4.0 | 2.7 | 2.0 | 4.4 | 3.8 | 4.1 | 4.3 | 4.2 |
| $Na_2O$ | | | | | | | | | 2.0 | | | | 0.1 | 1.0 | 0.1 | 0.1 | 0.1 | 0.1 | | |
| SrO | | | | | | 2.0 | | | | | | | | | 2.0 | | | | | |
| BaO | | | 2.0 | | | | | 2.0 | | | | | | | 2.0 | | | | | |
| CaO | | | | | | | | 2.0 | | | | | | | 1.0 | | | | | |
| $Li_2O$ | 15.3 | 17.0 | 13.0 | 15.0 | 15.5 | 15.2 | 15.1 | 15.4 | 15.1 | 15.1 | 15.0 | 14.5 | 14.8 | 15.0 | 14.0 | 16.0 | 16.0 | 15.0 | 15.1 | 14.9 |
| $Al_2O_3$ | 1.1 | 1.1 | 4.0 | 5.0 | 1.1 | 1.1 | 1.1 | 1.1 | 3.0 | 1.1 | 1.1 | 1.1 | 1.1 | 3.0 | 4.1 | 1.8 | 1.1 | 1.1 | 0.0 | 0.0 |
| $P_2O_5$ | 3.8 | 3.8 | 3.8 | 3.8 | 3.8 | 3.8 | 3.8 | 3.8 | 5.0 | 3.8 | 2.0 | 3.8 | 3.8 | 3.5 | 3.8 | 3.8 | 3.8 | 3.8 | 3.8 | 3.8 |
| MgO | 1.0 | 0.0 | 1.0 | 0.0 | 5.0 | 1.0 | 1.0 | 1.0 | 0.0 | 1.0 | 0.9 | 1.0 | 0.5 | 0.1 | 0.0 | 0.3 | 0.1 | 0.1 | 1.0 | 1.0 |
| $ZrO_2$ | | | | | | | | | | 2.0 | | 1.0 | 0.1 | 0.1 | 0.1 | 0.1 | 0.1 | 0.1 | | |
| ZnO | 5.2 | 0.7 | 6.0 | 3.9 | 0.0 | 3.6 | 4.1 | 2.4 | 4.3 | 3.2 | 6.0 | 2.8 | 4.7 | 5.2 | 4.0 | 2.0 | 4.5 | 4.8 | 5.1 | 5.0 |
| $TiO_2$ | | | | | | | | | | | | | | | | | | 1.6 | | |
| $V_2O_5$ | | | | | | | | | | | | | 0.2 | | | | | | | |
| $Fe_2O_3$ | | | | | | | | | | | | | | | | | | 0.2 | | |
| $MnO_2$ | | | | | | | | | | | | | | | | | | 0.5 | | |
| $CeO_2$ | | | 2.0 | | | | | | | | | 0.5 | 2.0 | 1.0 | 0.4 | 1.0 | 0.4 | 0.5 | | |
| $Y_2O_3$ | | | | | | | | | | | | | | | | | | | 2.4 | |
| $La_2O_3$ | | | | | | | | | | | | 0.5 | 0.3 | | 1.0 | 0.1 | 0.1 | 0.3 | | 3.4 |
| $Pr_2O_3$ | | | | | | | | | | | | 1.0 | | | | | | | | |
| $Ta_2O_5$ | | | | | | | | | | | | 1.5 | | | | | | | | |
| $Tb_4O_7$ | | | | | | | | | | | | 1.5 | 0.5 | | 0.5 | 0.5 | | | | |
| $Er_2O_3$ | | | | | | | | | | | | 1.0 | 0.3 | | | | | | | |
| | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |

TABLE IV

| Ex. No. | 1 | 2 | 3 | 4 | 5 | 6 | 7 | 8 | 9 | 10 |
|---|---|---|---|---|---|---|---|---|---|---|
| phases present after 1st crystallisation | LS | LS, LS2 | LS | LS | LS, LS2 | LS | LS | LS, LS2 | LS | LS |
| phases present after 2nd crystallisation | LS2, LP | LS2, LP | LS2, LP | LS2, LP | LS2, LP | lS2, LP | LS2, LP | LS2, LP | LS2, LP | LS2, LP |
| biaxial strength after 2nd crystallisation | 359 | 424 | 250 | 314 | 324 | 472 | 426 | 404 | 356 | 319 |
| biaxial solidification factor | 3.0 | 2.4 | 2.5 | 3.4 | 2.4 | 3.5 | 3.5 | 2.3 | 3.2 | 2.7 |
| KIC [$MPm^{0.5}$] after 2nd crystallisation | 1.6 | 2.2 | 1.9 | 1.9 | 1.8 | 2.3 | 1.8 | 2.4 | 1.9 | 1.8 |
| KIC solidification factor | 1.8 | 1.7 | 2.6 | 2.5 | 1.6 | 2.4 | 2.0 | 1.9 | 1.9 | 1.8 |
| grinding time in comparison to ProCAD | 93% | 103% | 95% | 89% | 98% | 93% | 94% | 105% | 94% | 94% |
| machinability | very good | good | very good | very good | good | very good | very good | good | very good | very good |
| edge strength | good | very good | good | good | good | good | acceptable | good | acceptable | good |
| translucency | very good | n.m. | n.m. | n.m. | n.m. | extraordinary | n.m. | n.m. | acceptable | n.m. |
| chemical durability (ISO 6872) | good | good | good | good | good | good | good | good | good | good |

| Ex. No. | 11 | 12 | 13 | 14 | 15 | 16 | 17 | 18 | 19 | 20 |
|---|---|---|---|---|---|---|---|---|---|---|
| phases present after 1st crystallisation | LS, LS2 | LS | LS | LS | LS | LS | LS | LS | LS2 | LS2 |
| phases present after 2nd crystallisation | LS2, LP | LS2, LP | LS2, LP | LS2, LP | LS2, LP | LS2, LP | LS2, LP | LS2, LP | LS2, LP | LS2, LP |
| biaxial strength after 2nd crystallisation | 301 | 354 | 381 | 389 | 342 | 329 | 420 | 387 | 440 | 405 |
| biaxial solidification factor | 1.7 | 2.9 | 3.0 | 3.1 | 2.6 | 2.9 | 3.2 | 3.4 | 2.2 | 2.1 |
| KIC [$MPm^{0.5}$] after 2nd crystallization | 2.1 | 2.0 | 1.9 | 2.0 | 1.8 | 1.7 | 2.1 | 1.9 | 1.8 | 1.9 |

TABLE IV-continued

| KIC solidification factor | 1.6 | 1.9 | 2.1 | 1.8 | 2.0 | 1.6 | 2.2 | 1.9 | 1.0 | 1.5 |
|---|---|---|---|---|---|---|---|---|---|---|
| grinding time in comparison to ProCAD | 115% | 98% | 90% | 91% | 94% | 100% | 95% | 94% | 119% | 129% |
| machinability | acceptable | very good | very good | very good | very good | good | good | very good | poor | poor |
| edge strength | good | acceptable | very good | very good | very good | very good | very good | good | good | good |
| translucency | n.m. | n.m. | n.m. | n.m. | n.m. | n.m. | n.m. | n.m. | n.m. | n.m. |
| chemical durability (ISO 6872) | good | good | good | good | good | good | good | good | good | good |

Table V shows the flexural strength and the fracture toughness for the machinable condition and the heat treated condition. Although the higher strengths of 200 and 193 of the metasilicate were shown having poor machinability, it has been found that such strengths and higher, in combination with low fracture toughness prove to have good machinability, especially for use with ultrasonic type machining and when using fluted tools.

TABLE V

| Example | Flexural Strength, MPa | | | | Fracture Toughness (KIc), MPaxm$^{1/2}$ | | | |
|---|---|---|---|---|---|---|---|---|
| | Final[1] | Machinable Condition[2] | SF[3] | Machinability by Cerec[7] | Final[4] | Machinable Condition[5] | KIcF[6] | Edge Strength |
| 1 | 359 | 120 | 3.0 | very good | 1.6 | 0.9 | 1.8 | good |
| 2 | 424 | 177 | 2.4 | good | 2.2 | 1.3 | 1.7 | very good |
| 3 | 250 | 100 | 2.5 | very good | 1.9 | 0.7 | 2.6 | good |
| 4 | 314 | 92 | 3.4 | very good | 1.9 | 0.8 | 2.5 | good |
| 5 | 324 | 135 | 2.4 | good | 1.8 | 1.1 | 1.6 | good |
| 6 | 472 | 135 | 3.5 | very good | 2.3 | 1.0 | 2.4 | good |
| 7 | 426 | 122 | 3.5 | very good | 1.8 | 0.9 | 2.0 | acceptable |
| 8 | 404 | 176 | 2.3 | good | 2.4 | 1.3 | 1.9 | good |
| 9 | 356 | 111 | 3.2 | very good | 1.9 | 1.0 | 1.9 | acceptable |
| 10 | 319 | 118 | 2.7 | very good | 1.8 | 1.0 | 1.8 | good |
| 11 | 301 | 177 | 1.7 | acceptable | 2.1 | 1.3 | 1.6 | good |
| 12 | 354 | 122 | 2.9 | very good | 2 | 1.1 | 1.9 | acceptable |
| 13 | 381 | 127 | 3.0 | very good | 1.9 | 0.9 | 2.1 | very good |
| 14 | 389 | 125 | 3.1 | very good | 2 | 1.1 | 1.8 | very good |
| 15 | 342 | 132 | 2.6 | very good | 1.8 | 0.9 | 2.0 | very good |
| 16 | 329 | 113 | 2.9 | good | 1.7 | 1.1 | 1.6 | very good |
| 17 | 420 | 131 | 3.2 | good | 2.1 | 1.0 | 2.2 | very good |
| 18 | 387 | 114 | 3.4 | very good | 1.9 | 1.0 | 1.9 | good |
| 19 | 440 | 200 | 2.2 | poor | 1.8 | 1.8 | 1.0 | good |
| 20 | 405 | 193 | 2.1 | poor | 1.9 | 1.3 | 1.5 | good |

[1]Final is the strength of the disilicate system.
[2]Machinable Condition is the strength of the metasilicate system.
[3]SF is the biaxial strength solidification factor.
[4]Final is the fracture toughness of the disilicate system.
[5]Machinable Condition is the fracture toughness of the metasilicate system.
[6]KIcF is the fracture toughness solidification factor.
[7]Machinability given in this table is only for Cerec 3 (Sirona) and may be even better for larger CAD/CAM system.

The data in Table II show that the lithium metasilicate glass ceramics combine a very good machinability and high edge strength with the easy possibility to convert them by a simple heat treatment into lithium disilicate glass ceramics which have a very high bending strength as well as an excellent chemical durability and good translucence, all of which being properties which make them very attractive as materials useful for the manufacture of dental restorations.

In the following some examples are described in more detail:

Example 1

The glass was molten at a temperature of 1500° C. for 3 hours and was then poured into steel moulds which were preheated to 300° C. After one minute the glass bars were transferred into a cooling furnace and were tempered at 500° C. for 10 minutes and then cooled to room temperature.

The glass was homogeneous and transparent.

Following the glass bar was subjected to a first crystallization at 650° C. for a period of 20 minutes.

From the such ceramized bar, discs were sawn out of a round bar, and biaxial strength was measured. The phase content was analyzed via XRD (X-ray diffraction). Lithium metasilicate was the only phase that was detected. Biaxial strength was 119+/−25 MPa.

Also the milling time of test bodys was measured. The milling time of the test body was one minute below that of ProCAD®, which was used as reference.

The edge strength was good.

Additional 10 discs were subjected to a second crystallization at 850° C. for a period of 10 minutes and biaxial strength and fracture toughness were measured.

Biaxial strength was 359+/−117 MPa which correlates to a solidification factor of 3.0.

Fracture toughness (IF) was 1.6 MPam$^{0.5}$.

Translucence was very good.

The chemical stability according to ISO 6872 (4% acetic acid, 80° C., 16 h) was 37 pg/cm$^2$.

Example 6

Glass bars were produced according to example 1. The glass again was homogeneous and transparent.

The first crystallization was performed at 650° C. for a period of 20 minutes.

Lithium metasilicate was determined to be the main phase with traces of lithium disilicate also being present. Biaxial strength was 135+/−24 MPa.

Again the milling time of a test body was measured. The milling time of the test body was one minute below that of ProCAD®, which again was used as reference.

The edge strength was very good.

After a second crystallization which was performed according to example 1 the biaxial strength was 472+/−85 MPa which correlates to a solidification factor of 3.5.

Fracture toughness (IF) was 2.3 MPam$^{0.5}$.

Translucence was extraordinary.

Example 9

Glass bars were produced according to example 1. The glass again was homogeneous and transparent.

The first crystallization was performed at 650° C. for a period of 20 minutes.

Lithium metasilicate was determined to be the only phase. Biaxial strength was 112+/−13 MPa.

Again the milling time of a test body was measured. The milling time of the test body was one minute below that of ProCAD®, which again was used as reference.

The edge strength was good.

After a second crystallization which was performed according to example 1 the biaxial strength was 356+/−96 MPa which correlates to a solidification factor of 3.16.

Fracture toughness (IF) was 1.9 MPam$^{0.5}$.

Translucence was acceptable.

Example 20 (Comparison)

Glass bars were produced according to example 1. The glass again was homogeneous and transparent.

The first crystallization was performed at 650° C. for a period of 20 minutes.

Lithium disilicate was determined as the main phase and lithium metasilicate was only present in traces. Biaxial strength was 194+/−35 MPa.

Again the milling time of a test body was measured. The milling time of the test body was four minutes longer that of ProCAD®, which again was used as reference.

The edge strength was poor.

After a second crystallization which was performed according to example 1 the biaxial strength was 405+/−80 MPa which correlates to a solidification factor of 2.09.

Fracture toughness (IF) was 1.88 MPam$^{0.5}$.

Translucence was very good.

This example makes it even more obvious that in the light of the glass ceramic materials according to the invention the adverse properties in respect to machinability of the prior art material disqualify same to be used in applications as are mentioned above.

The following examples 21 to 23 show the usefulness of the lithium silicate glass according to the invention which comprises nuclei suitable for the formation of lithium metasilicate and subsequently lithium disilicate glass ceramics.

Example 21

A glass melt having the composition according to example 14 was melted in a platinum crucible at a temperature of 1500° C. for 3 hours. The glass was not poured in a steel mould, but quenched in water.

Thus, a glass granulate formed which was dried and subsequently heated to 500° C. for 30 minutes to produce nuclei suitable for the formation of lithium metasilicate crystals. The obtained glass was milled to a particle size of less than 45 pm.

The obtained powder was mixed with a modeling liquid consisting of more than 95% water and additives for improving moldability and layered on a crown cap of densely sintered zirconium oxide, e.g. DCS-zircon.

The crown cap was fired in a dental furnace at a temperature of 900° C. with 2 minutes holding time. By this procedure the applied glass powder containing nuclei for the crystallization was simultaneously crystallized and densely sintered so that a dentine core of lithium disilicate glass ceramic resulted. On this core a suitable incisal mass having a suitable expansion coefficient was applied.

The final anterior tooth restoration showed good resistance against rapid temperature changes up to 160° C. This proves a good bond between the dentine layer of lithium disilicate glass ceramic and the framework of high-strength zirconium oxide.

Example 22

Bars of a glass having a composition according to example 14 were prepared in the same manner as in example 1. The glass bars were homogenous, transparent and light yellow coloured. A crown cap of densely-sintered zirconium oxide was circularly reduced. Subsequently a dentine core was layered with dental wax and the crown margin was modeled on the stump. The restoration was provided with a cast-on channel. The crown cap was applied on a muffle basis and embedded in investment material, (Empress Speed, Ivoclar). After the required binding time the muffle was preheated to 850° C. resulting in the removal of the wax. After 90 minutes a blank of the above lithium silicate glass having nuclei for forming lithium metasilicate was put in the muffle and pressed on the cap of zirconium oxide in accordance with the known Empress-hot pressing process at 900° C. This resulted in crystallization of the glass blank to a lithium disilicate glass ceramic.

After divesting, the final product was a zirconium oxide cap having a dentine layer of lithium disilicate glass ceramic. This dental restoration showed an excellent fit of the circular edge on the model. Furthermore, the so-prepared dentine layer was free from porosities.

Example 23

A metal cap of an alloy having an expansion coefficient of 12.8*10$^{-6}$ 1/K and a solidification temperature of 11000° C. was prepared in a cast process, sand-blasted and by an oxidation-firing step prepared for the further processing.

In an analogous manner as in example 22 a dentine core was applied on the cap using modeling wax. The metal cap was embedded, and the wax was removed by firing in a furnace. As in example 22 a blank of the lithium silicate glass having suitable nuclei was hot-pressed on the metal cap at 900° C.

The so-prepared dental restoration showed a good bond between metal framework and the lithium disilicate glass ceramic and also had a high resistance against drastic temperature changes of above 160° C.

TABLE VI

|  | Example 24 | Example 25 |
| --- | --- | --- |
| $SiO_2$ | 70.9 wt.-% | 70.4 wt.-% |
| $Li_2O$ | 14.7 | 14.6 |
| $K_2O$ | 4.7 | 4.0 |
| $P_2O_5$ | 3.3 | 3.2 |
| $Al_2O_3$ | 1.4 | 3.4 |
| $ZrO_2$ | 1.0 | 0.8 |
| $CeO_2$ | 2.0 | 2.0 |
| ZnO | 0.6 | — |
| $Er_2O_3$ | 0.6 | 0.6 |
| $Tb_4O_7$ | 0.5 | 0.5 |
| $V_2O_5$ | 0.3 | 0.3 |
| MgO | — | 0.3 |
| Melting | 1500° C./2 h | 1500° C./2 h |
| Nucleation | 500° C./10 min | 500° C./10 min |
| Crystallization | 660° C./10 min | 670° C./10 min |
| Biaxial flex. Strength [MPa] | 297 ± 39 | 247 ± 42 |
| microstructure | Lithium metasilicate | Lithium metasilicate |
| Fracture toughness [$MPam^{0.5}$] | 1.20 ± 0.12 | — |

Examples 24 and 25 show results for lithium metasilicate having high flexural strength (in the range of about 300 MPa) in combination with a low fracture toughness of 1.0 to 1.4 $MPam^{0.5}$. It has been realized that, due to the relatively low fracture toughness and hardness, the metasilicate blocks having high strengths can be machined within good time ranges per unit, using CAD/CAM systems such as DCS Precimill (DCS Switzerland) or Roeders 5-axis CNC machines (ROEDERS GmbH, Germany). The milling times range from less than about 45 minutes per unit, preferably 30 minutes or less and most preferably 15 minutes or less per unit, wherein unit is crown, partial crown, pontic, abutment, inlay or onlay.

Examples 26 to 33

A total of 8 different lithium metasilicate glass ceramics according to the invention with the chemical compositions given in Table VII were prepared using the indicated second heat treatment. The obtained glass ceramics were then converted to the corresponding lithium disilicate glass ceramics using the indicated third heat treatment.

Firstly, samples of the corresponding starting glasses were melted in a platinum-rhodium crucible at a temperature of 1450° C. and for a period of 40 minutes. The glass melt was poured into water and the obtained granules were, after drying, again melted at 1500° C. The glass melts obtained were then poured into graphite moulds to give blocks. After relaxation of the glass blocks at 500 to 600° C. for 10 minutes to 3 hours, they were subjected to the given second heat treatment. Before effecting the third heat treatment, the blocks were checked for their machinability by milling in a CAD-CAM milling machine (i.e. CEREC 3®). Finally, the indicated third heat treatment was conducted. The crystal phases present after the second and third heat treatment were identified by XRD techniques and are given in table VII.

Further, the opalescence of the products was visually assessed and the contrast value CR was determined according to BS 5612 (British Standard) using a spectral colorimeter (Minolta CM-3700d). The chemical stability in acetic acid was determined as well as the stability in artificial saliva. The corresponding data are to be found in the following Table VIII and show in particular the surprising combination of a lack of opalescence together with a high translucence and stability. The composition of the artificial saliva is given in Table IX.

The data obtained show that the lithium metasilicate glass ceramics according to the invention combine a very good machinability and high edge strength with the easy possibility to convert them by a simple heat treatment into lithium disilicate glass ceramics which have a very high bending strength as well as an excellent chemical durability and good translucence, all of which being properties which make them very attractive as materials useful for the manufacture of dental restorations.

Examples 34 to 37

Four glass ceramics according to the invention were prepared in analogous manner as examples 26 to 33. However, the heat treatment scheme was different. In addition each material was subjected to the schemes referred to as "Cycle A" and "Cycle B" which differ in the temperature used for the crystallization of lithium metasilicate, namely 650° and 700° C., respectively. Strengths were measured for both Cycles A and B after crystallization of lithium metasilicate (heat treatment 2) and after crystallization of lithium disilicate (heat treatment 3).

Details as to the materials prepared and tested as well as their properties are given in the table X. It is apparent that the "Cycle B" treatment using a temperature of 700° C. for the crystallization of lithium metasilicate leads to lithium disilicate glass ceramics having excellent strengths.

TABLE VII

| | Example | | | | | | | |
| --- | --- | --- | --- | --- | --- | --- | --- | --- |
| | 26 | 27 | 28 | 29 | 30 | 31 | 32 | 33 |
| Molar ratio | | | | | | | | |
| SiO2: Li2O | 2.39:1 | 2.39:1 | 2.4:1 | 2.39:1 | 2.39:1 | 2.39:1 | 2.39:1 | 2.39:1 |
| Al2O3:K2O | 1:1.0 | 1:1.0 | 1:1.2 | 1:1.20 | 1:1.35 | 1:1.50 | 1:1.70 | 1:1.30 |
| | wt.-% (Mol %) | wt.-% (Mol %) | wt.-% (Mol %) | wt.-% (Mol %) | wt.-% (Mol %) | wt.-% (Mol %) | wt.-% (Mol %) | wt.-% (Mol %) |
| SiO2 | 72.21 (66.12) | 70.64 (65.62) | 70.52 (65.52) | 70.78 (65.57) | 70.78 (65.56) | 70.78 (65.56) | 70.78 (65.55) | 70.78 (65.29) |
| K2O | 3.16 (1.85) | 3.09 (1.83) | 3.81 (2.26) | 3.76 (2.22) | 3.96 (2.34) | 4.16 (2.46) | 4.36 (2.58) | 3.36 (1.98) |
| Li2O | 14.99 (27.60) | 14.68 (27.43) | 14.64 (27.35) | 14.7 (27.38) | 14.7 (27.38) | 14.7 (27.37) | 14.7 (27.37) | 14.7 (27.26) |
| Al2O3 | 3.45 (1.86) | 3.38 (1.85) | 3.35 (1.83) | 3.38 (1.85) | 3.18 (1.74) | 2.98 (1.63) | 2.78 (1.52) | 2.78 (1.51) |
| P2O5 | 3.28 (1.27) | 3.21 (1.26) | 3.2 (1.26) | 3.21 (1.26) | 3.21 (1.26) | 3.21 (1.26) | 3.21 (1.26) | 3.21 (1.25) |
| ZrO2 | 2.91 (1.30) | 3.00 (1.36) | 2.5 (1.13) | 1.8 (0.81) | 1.8 (0.81) | 1.80 (0.81) | 1.8 (0.81) | 1.8 (0.81) |
| CeO2 | | 1.88 (0.61) | 1.86 (0.60) | 2.00 (0.65) | 2.00 ( 0.65) | 2.00 (0.65) | 2.00 (0.65) | 2.00 (0.65) |
| V2O5 | | 0.12 (0.04) | 0.12 (0.04) | 0.07 ((0.02) | 0.07 ((0.02) | 0.07 ((0.02) | 0.07 (0.02) | 0.07 (0.02) |
| MnO2 | | | | 0.03 (0.02) | 0.03 (0.02) | 0.03 (0.02) | 0.03 (0.02) | 0.03 (0.02) |

TABLE VII-continued

| | | | | | | | | |
|---|---|---|---|---|---|---|---|---|
| Er2O3 | | | | 0.12 (0.017) | 0.12 (0.017) | 0.12 (0.017) | 0.12 (0.017) | 0.12 (0.017) |
| MgO | | | | 0.15 (0.21) | 0.15 (0.21) | 0.15 (0.21) | 0.15 (0.21) | 0.15 (0.21) |
| CaO | | | | | | | | 1.00 (0.99) |
| Crystalline phases after: | | | | | | | | |
| Second heat treatment: 20'/650° C. | Li2SiO3 Li2Si2O5* | Li2SiO3 Li2Si2O5* | Li2SiO3 | Li2SiO3 | | Li2SiO3 | Li2SiO3 | Li2SiO3 Li2Si2O5* |
| Third heat treatment: 10'/850° C. | Li2Si2O5 Li3PO4* | Li2Si2O5 Li3PO4* | Li2Si2O5 Li3PO4* | Li2Si2O5 Li3PO4* | Li2Si2O5 Li3PO4* | Li2Si2O5 Li3PO4* | Li2Si2O5 Li3PO4* | Li2Si2O5 Li3PO4* |

TABLE VIII

| Example | 26 | 27 | 28 | 29 | 30 |
|---|---|---|---|---|---|
| CR-Value BS-5612 (1978) | 40.4 | 37.0 | 50.0 | 59.3 | 58.8 |
| Opalescence | No | No | No | No | No |
| Chemical stability in Acetic acid (24 h/80° C., mass loss in µg/cm$^2$) | 9 | 18 | 48 | 3 | 9 |
| Chemical stability in Saliva (7 d/60° C., mass loss in µg/cm$^2$) | 13 | 17 | 28 | 27 | 17 |

TABLE IX

Composition of artificial saliva

| Component | Amount in mg in a total of 500 ml H$_2$O |
|---|---|
| NaCl | 125.64 |
| KCl | 963.9 |
| NH$_4$Cl | 178.0 |
| CaCl$_2$·2H$_2$O | 227.8 |
| KSCN | 189.2 |
| CO(NH$_2$)$_2$ | 200.0 |
| Na$_2$SO$_4$·10H$_2$O | 336.2 |
| NaHCO$_3$ | 630.8 |
| KH$_2$PO$_4$ | 654.5 |

TABLE X

| Example | 34 | 35 | 36 | 37 |
|---|---|---|---|---|
| SiO$_2$ | 74.37 | 72.89 | 72.21 | 71.40 |
| K$_2$O | 3.26 | 3.18 | 3.16 | 3.13 |
| Li$_2$O | 15.44 | 15.13 | 14.99 | 14.79 |
| Al$_2$O$_3$ | 3.55 | 3.48 | 3.45 | 3.41 |
| P$_2$O$_5$ | 3.38 | 3.31 | 3.28 | 3.22 |
| ZrO$_2$ | 0.00 | 2.01 | 2.91 | 4.05 |
| | All values above in wt.-% | | | |
| SiO$_2$:Li$_2$O (Mol.-ratio %) | 2.39 | 2.40 | 2.39 | 2.40 |
| Cycle A: | (1) 500° C./10 min + (2) 650° C./20 min + (3) 850° C./10 min *) | | | |
| Biaxial Flexural Strength/MPa after heat treatment (2) | 260 +/− 38 | 284 +/− 35 | 270 +/− 20 | 240 +/− 13 |
| Biaxial Flexural Strength/MPa after heat treatment (3) | 786 +/− 92 | 515 +/− 54 | 522 +/− 82 | 479 +/− 36 |
| Contrast Ratio | 0.80 | 0.56 | 0.43 | 0.36 |
| Cycle B: | (1) 500° C./10 min + (2) 700° C./20 min + (3) 850° C./10 min *) | | | |
| Biaxial Flexural Strength/MPa after heat treatment (2) | 270 +/− 36 | 290 +/− 59 | 235 +/− 40 | 232 +/− 44 |
| Biaxial Flexural Strength/MPa after heat treatment (3) | 828 +/− 104 | 659 +/− 75 | 608 +/− 90 | 694 +/− 113 |
| Contrast Ratio | 0.83 | 0.63 | 0.53 | 0.41 |

*)
(1) Nucleation in the glass
(2) Crystallization of Li-Metasilicate
(3) Crystallization of Li-Disilicate from Li-Metasilicate Tool wear is another very important factor as diamond or diamond coated tools are very expensive. Faster milling is normally associated with increased tool wear. The milling times provided above are based on tool life span of at least ten units per conventional diamond tool such as diamond plated burr of any shape and size. This will translate into at least 5 hours of milling time or preferably 10 hours for a new conventional tool before it needs to be replaced. There are technologies and milling tools available that are synergetic with lithium silicate glass-ceramic materials of the present invention such as ultrasonically aided machining and also use of fluted diamond coated tools such as end-mills and microend-mills coated with various continuous diamond coatings or other hard coatings, both amorphous and crystalline such as different types of CVD, PVD or plasma coatings.

Flexural or biaxial strength is measured in accordance with ISO 6872:2008, which is included by reference herein. Flexural strength under ISO 6872:2008 is comparable to biaxial strength, three-point bend strength and four-point bend strength. Milling, grinding, machining, cutting are used interchangeably to denote subtractive shaping processes Singular form of terms may also include plural forms of the same term such as, for example, wherein machinable phase also includes a combination of various phases, such phase assemblage also being machinable.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. A process for manufacturing a lithium silicate dental glass-ceramic article comprising: preparing a lithium silicate blank comprising lithium metasilicate as the main crystalline phase and exhibiting a flexural strength of greater than 180 MPa; machining the lithium silicate blank into a dental article; and heat treating the machined dental article in the temperature range of from about 700° C. to about 900° C. to close surface flaws, and optionally, coating with a glass or glass ceramic by sintering or hot pressing.

2. A process for manufacturing a lithium silicate dental glass-ceramic article comprising: preparing a lithium silicate blank comprising lithium metasilicate as the main crystalline phase and exhibiting a flexural strength of greater than 180 MPa; machining the lithium silicate blank into a dental article; and applying a coating thereon, wherein the coating is applied by sintering or pressing and the coating comprises glass or a glass ceramic.

3. A process for the preparation of a lithium silicate blank, which comprises:

producing a melt of a starting glass containing the initial components 64.0-73.0% by weight $SiO_2$, 13.0-17.0% by weight $Li_2O$, 2.0-5.0% by weight $K_2O$, 0.5-5.0% by weight $Al_2O_3$ and 2.0-5.0% by weight $P_2O_5$ or other nucleation agent as the main components, pouring the melt of the starting glass into a mold to form a starting glass blank, subjecting the starting glass blank to heat treatment to obtain the lithium silicate blank with lithium metasilicate crystals as the main crystalline phase by heating the glass blank to a temperature in the range from about 450° C. to about 700° C. for a time between about 5 minutes and about 1 hour, and cooling the lithium silicate blank having the lithium metasilicate crystals as the main crystalline phase.

4. A process for manufacturing a lithium silicate dental glass-ceramic article comprising: preparing a lithium silicate blank comprising lithium metasilicate as the main crystalline phase and exhibiting a flexural strength of greater than 180 MPa; machining the lithium silicate blank into a dental article; and further finishing the dental article by staining, glazing, or veneering the dental glass-ceramic with an overlay porcelain and firing in the temperature range of from about 350° C. to about 850° C.

* * * * *